(12) United States Patent
Landuyt et al.

(10) Patent No.: US 8,735,329 B2
(45) Date of Patent: May 27, 2014

(54) MARKERS AND DIAGNOSTIC METHODS FOR METASTASIS

(75) Inventors: Bart Landuyt, Landen (BE); Liliane Schoofs, Kessel-lo (BE); Walter Luyten, Bertem (BE)

(73) Assignee: Katholieke Universiteit Leuven K.U. Leuven R&D, Leuven (BE)

( * ) Notice: Subject to any disclaimer, the term of this patent is extended or adjusted under 35 U.S.C. 154(b) by 901 days.

(21) Appl. No.: 12/735,433

(22) PCT Filed: Jan. 19, 2009

(86) PCT No.: PCT/EP2009/050572
§ 371 (c)(1),
(2), (4) Date: Jul. 16, 2010

(87) PCT Pub. No.: WO2009/090269
PCT Pub. Date: Jul. 23, 2009

(65) Prior Publication Data
US 2010/0284935 A1      Nov. 11, 2010

(30) Foreign Application Priority Data

Jan. 18, 2008   (GB) .................................. 0800944.1
Jul. 4, 2008    (GB) .................................. 0812298.8

(51) Int. Cl.
C40B 30/04            (2006.01)

(52) U.S. Cl.
USPC ............................................................ 506/9

(58) Field of Classification Search
None
See application file for complete search history.

(56) References Cited

U.S. PATENT DOCUMENTS

2007/0099209 A1*   5/2007   Clarke et al. ...................... 435/6

* cited by examiner

*Primary Examiner* — Heather Calamita
*Assistant Examiner* — Christian Boesen
(74) *Attorney, Agent, or Firm* — Amster, Rothstein & Ebenstein LLP

(57) ABSTRACT

The present invention provides methods for the prediction, prognosis and/or diagnosis of metastasis. The present invention also provides proteins (or the related nucleic acid sequences) or protein expression profiles which are predictive and/or prognostic for metastasis. The invention thus relates to the use of said proteins and the corresponding amino acid or nucleic acid sequences for the prediction, prognosis or diagnosis of metastasis.

16 Claims, 1 Drawing Sheet

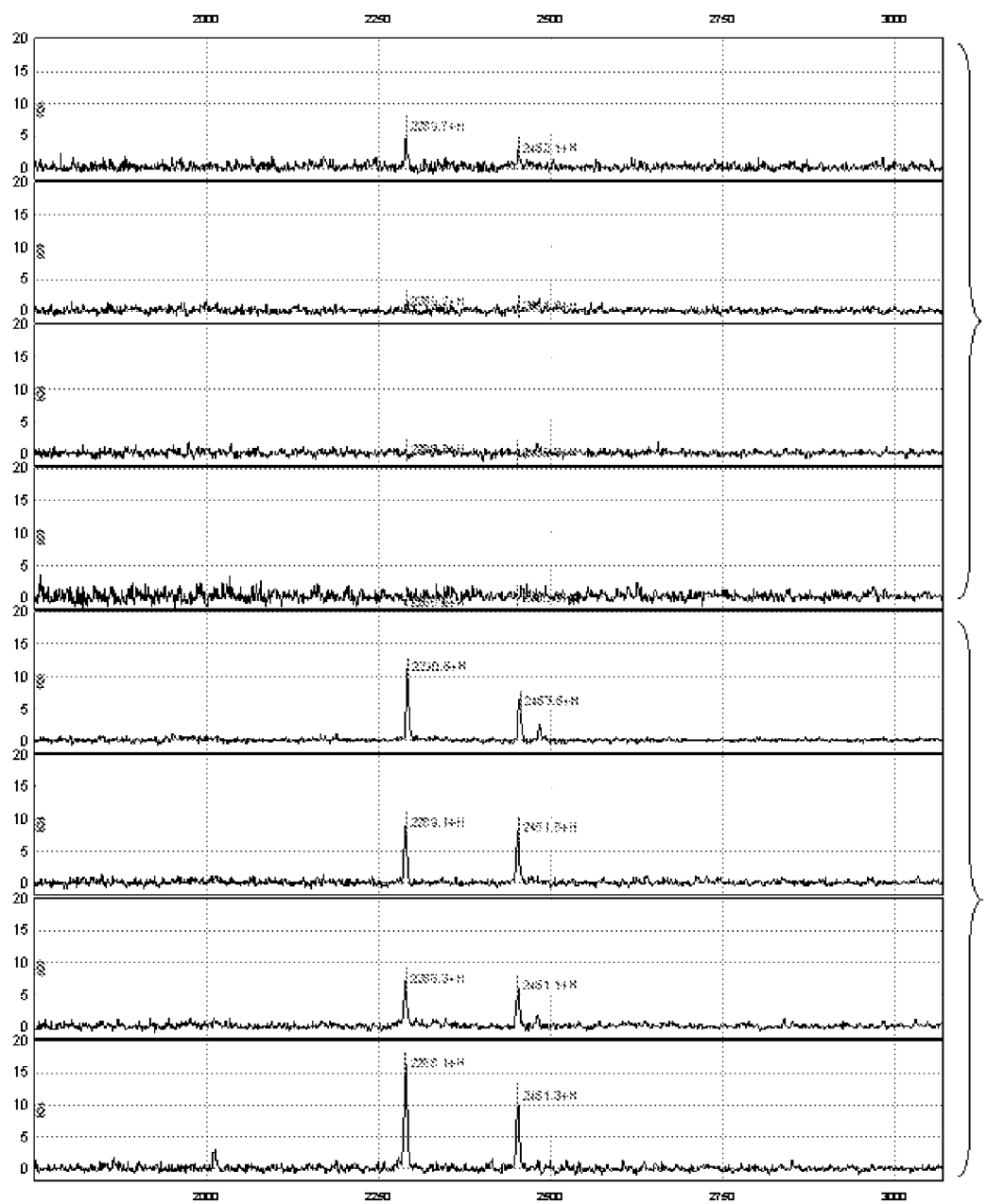

MARKERS AND DIAGNOSTIC METHODS FOR METASTASIS

This is a U.S. national phase of PCT Application No. PCT/EP2009/050572, filed Jan. 19, 2009, which claims the benefit of Great Britain Application Nos. 0800944.1, filed Jan. 18, 2008 and 0812298.8, filed Jul. 4, 2008.

FIELD OF THE INVENTION

The present invention relates to the prediction, prognosis or diagnosis of metastasis, more particularly in patients with breast cancer. Proteins have been identified which can be used for the diagnosis of metastasis, more particularly for the prediction of the involvement of the lymph nodes in breast cancer patients.

BACKGROUND OF THE INVENTION

The extent of lymph node (LN) metastasis is a major determinant for the staging and the prognosis of most human malignancies and often guides therapeutic decisions.

For instance, for breast cancer, in current clinical practice, axillary lymph node involvement, age of the patient, tumour size, pathologic grade and hormone receptor status are considered as the main prognostic and/or predictive factors (Dikicioglu E. et al. 2005, *Int. J. Clin. Pract.* 59:1039-1044). Involvement of lymph nodes and the number of lymph nodes harbouring metastases have an inverse relationship with the disease prognosis, meaning that patients with lymph nodes free of metastases have a better outcome (Weigelt B. et al. 2004 *Br. J. Cancer* 90:1531-1537).

Till now, surgery is the only accurate method to identify axillary lymph node metastases. Until recently, the standard treatment for patients with operable breast cancer included the complete axillary lymph node dissection. More than half of these patients were found to have metastases-free lymph nodes and thus had been subjected to unnecessary morbidity (Harris J. R. et al. 2000 Second edition. Lippincott Williams and Wilkins, Philadelphia, p 413). The performance of selective sentinel lymph node dissection can overcome the sequelae of axillary lymph node dissection (Rietman J. S 2004 *Ann. Surg. Oncol.* 11:1018-1024), but is only indicated in a selected group of patients (Kuehn T. et al. 2005 *Cancer* 103:451-461). A less invasive method for the assessment of lymph node status is the sentinel lymph node biopsy (SLNB). Thereby, the lymphatic route of tumour cells to the lymph node(s) that primarily drains the tumour and most likely harbours metastatic disease are mapped (Giuliano A. E. et al. Ann Surg 1994, 220, 391-401).

Because lymph node involvement remains a critical benchmark in cancers such as breast cancer and is often the earliest sign of tumour progression, insights into the underlying molecular mechanisms are essential. Lymph node metastasis is a complex series of events involving the generation of new blood vessels, growth, invasion with breakdown of the host matrix, transport to other sites with adhesion and subsequent invasion (Shinozaki M. 2005 *Clin. Cancer Res.* 11:2156-2162). If the lymph node status can be predicted from primary cancer tissue, axillary surgery can be avoided in lymph node negative patients and for patients with isolated lymphatic drainage to non-axillary lymph nodes it will be the only way for accurate staging (and thus treatment).

The prior art also describes some methods for the prediction of the involvement of the lymph nodes without lymph node dissection or biopsy, such as the use of clinicopathologic characteristics (Nothingham Prognostic Index (NPI), includes the breast tumour diameter) the detection of altered glycosilation in the primary tumour (Brooks, S. A. et al. Lancet 1991, 338 (8759), 71-74) or of mRNA markers. However, these methods do not yield results with enough clinical significance and have other problems limiting their use in clinic.

Therefore, there is a huge need for the early, correct and easy diagnosis of lymph node involvement when tumours are identified.

SUMMARY OF THE INVENTION

The present invention relates to methods for the prediction, prognosis or diagnosis of the involvement of the lymph nodes in patients with cancer. More particularly the invention provides methods for the prediction, prognosis or diagnosis of the involvement of the axillary lymph node in patients with breast cancer.

In particular embodiments these methods involve determining the expression pattern of one or more proteins in a tissue sample obtained from a cancer patient with a reference expression pattern, whereby increased expression of one or more proteins compared to the reference is indicative of lymph node metastasis in the patient.

The present invention also provides proteins (as well as the related nucleic acid sequences) which can be used as markers for metastasis (also referred to as "predictive" or "marker" proteins, amino acid and nucleotide sequences herein) and protein expression profiles which are predictive or prognostic for metastasis in patients with cancer. More particularly, the present invention provides marker proteins (and the related nucleic acid sequences) and protein expression profiles which are predictive or prognostic for lymph node metastasis in patients with cancer, more particularly, breast cancer. The invention further relates to the use of said proteins and the corresponding amino acid or nucleic acid sequences or reagents specifically identifying said proteins or nucleic acid sequences for the prediction, prognosis or diagnosis of metastasis, more particularly lymph node metastasis. Furthermore, the present invention provides a method for the prediction of metastasis in cancer patients, by measuring the expression of said proteins tissues of said patients. In particular embodiments, such methods involve determining the abundance of said proteins in cancer tissue extracts and/or in the blood of said patients. More particularly, the present invention provides methods for the prediction of lymph node metastasis in breast cancer patients, by measuring the amount of said proteins in breast cancer tissue extracts or in the blood of these breast cancer patients.

In particular embodiments of the foregoing, methods for the prediction, prognosis or diagnosis of metastasis in patients with cancer are provided which involve the use of one or more proteins, nucleotide sequences encoding such proteins or reagents specifically identifying such proteins or nucleotide sequences, wherein the proteins are selected from the group consisting of Hemoglobin Chain alpha; Eosinophil peroxidase; Histone H4; 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088]. The methods of the invention may involve the use of two or more, more specifically three or more, four, five, six, seven, eight, nine, ten, eleven, twelve, thirteen, fourteen, fifteen, sixteen, seventeen, eighteen, nineteen, twenty, twenty one, twenty two or all twenty three of these proteins or nucleotide sequences encoding these proteins or reagents specifically identifying these proteins.

In particular embodiments the methods of the present invention for the prediction, prognosis or diagnosis of metastasis in patients with cancer involve the use of one or more amino acid sequences selected from the group consisting of EETRGVLKVFLENVIRDAVT [SEQ ID NO:1]; NIGYGSNKKTKHMLPSGFRKF [SEQ ID. NO:2]; WLPAEYEDGLSLPFGWTPSRR [SEQ ID. NO: 3]; VLSPADKTNVKAAWGKVGAHAGEYGAEALER-MFLSFPTTKTYFPHFDLSHGSAQV KGHGKKVADALT-NAVAHVDDMPNALSALSDLHAHKLRVDPVNFKLLS-HCLLVTLAA HLPAEFTPAVHASLDKFLASVSTV-LTSKYR [SEQ ID. NO:4] or the use of one or more nucleotide sequences encoding these amino acid sequences or reagents specifically identifying these amino acid sequences.

In further particular embodiments, the methods for the prediction, prognosis or diagnosis of metastasis in patients with cancer of the present invention as described above in addition comprise the use of Vascular Endothelial Growth Factor A isoform 111, a nucleotide sequence encoding Vascular Endothelial Growth Factor A isoform 111 or a reagent specifically identifying Vascular Endothelial Growth Factor A isoform 111. More specifically, such methods may involve the use of the amino acid sequence APMAEGGGQNH-HEWKFMDVYQRSYCHPIETLVDIFQEYP-DEIEYIFKPSCVPLMR CGGCCNDEGLECVPTEESNIT-MQIMRIKPHQGQHIGEMSFLQHNKCECRCDKPRR [SEQ ID. NO:5], or a nucleotide sequence encoding said sequence or a reagent specifically identifying said amino acid sequence.

In particular embodiments, the present invention provides for the use of one or more reagents specifically identifying:
  a protein selected from the group of Hemoglobin Chain alpha; Eosinophil peroxidase; Histone H4; 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088] or a nucleotide sequence encoding such a protein; and/or
  an amino acid sequence selected from the group of EETRGVLKVFLENVIRDAVT [SEQ ID NO:1]; NIGYGSNKKTKHMLPSGFRKF [SEQ ID. NO:2]; WLPAEYEDGLSLPFGWTPSRR [SEQ ID. NO:3]; VLSPADKTNVKAAWGKVGAHAGEYGA-EALERMFLSFPTTKTYFPHFDLSHG SAQVKGH-GKKVADALTNAVAHVDDMPNALSALSDL-HAHKLRVDPVNFKLLS HCLLVTLAAHLPAEFTPAVHASLDK-FLASVSTVLTSKYR [SEQ ID. NO:4], or a nucleotide sequence encoding such an amino acid sequence,
  in a method for the prediction, prognosis or diagnosis of metastasis in patients with cancer.

In particular embodiments the reagents capable of specifically identifying the proteins or amino acid sequences are antibodies. However, also other detection methods of said proteins or nucleotide sequences are envisaged, such as wherein microelectronic structures such as chips are used.

In further particular embodiments of the present invention methods are provided for the prediction, prognosis or diagnosis of metastasis of cancer in a patient, comprising determining the expression and/or measuring the concentration of at least one of the proteins described herein or of the corresponding amino acid or nucleic acid sequence in a biological sample isolated from said patient.

In particular embodiments, the present invention provides methods for the prediction, prognosis or diagnosis of the involvement of the axillary lymph node in patients with breast cancer, comprising determining the expression of and/or measuring the concentration of at least one of the proteins described herein or of the corresponding amino acid or nucleic acid sequence in a biological sample isolated from said breast cancer patient.

In particular embodiments of the invention the detection of said markers is performed in or with samples isolated from humans, more in particular from patients, more in particular from patients diagnosed as suffering from a cancer, such as breast cancer. Most particularly, the biological sample is a sample of tumour tissue isolated from the patient.

In particular embodiments, the methods of the invention comprise the measuring (directly or indirectly) the levels of one or more proteins in a sample isolated from a mammal, more in particular isolated from a patient diagnosed with cancer, yet more in particular the sample is from breast tumour tissue isolated from a patient with breast cancer. In further particular embodiments, methods are provided which further comprise comparing the measured level of one or more of the marker proteins with the average or reference levels as described herein.

In particular embodiments, methods for the prediction, prognosis or diagnosis of metastasis of cancer in a patient are provided which comprise measuring, directly or indirectly, the levels of one or more of the proteins selected from the group consisting of Hemoglobin Chain alpha; Eosinophil peroxidase; Histone H4; 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088]. In further particular embodiments the levels of at least 2, 3, 4, 5, 6, 7, 8, 9, 10, 11, 12, 13, 14, 15, 16, 17, 18, 19, 20, 21, 22 or all 23 of said proteins are determined.

More particularly, methods are provided which comprise measuring, directly or indirectly, the levels of one or more of the amino acid sequences depicted in Table 2 with numbers 9, 11, 12, and 28 (i.e. EETRGVLKVFLENVIRDAVT [SEQ ID NO:1]; NIGYGSNKKTKHMLPSGFRKF [SEQ ID. NO:2]; WLPAEYEDGLSLPFGWTPSRR [SEQ ID. NO:3]; VLSPADKTNVKAAWGKVGAHAGEYGAEALER-MFLSFPTTKTYFPHFDLSHGSAQV KGHGKKVADALT-NAVAHVDDMPNALSALSDLHAHKLRVDPVNFKLLS-HCLLVTLAA HLPAEFTPAVHASLDKFLASVSTV-LTSKYR [SEQ ID. NO:4]; Even more particularly the levels of two, three or all four of these amino acid sequences are determined.

In further particular embodiments of the methods of the present invention, the level of the protein in Table 2 with number 28 (i.e. APMAEGGGQNHHEWKFMDVYQRSY-CHPIETLVDIFQEYPDEIEYIFKPSCVPLMR CGGC- CNDEGLECVPTEESNITMQIMRIK-
PHQGQHIGEMSFLQHNKCECRCDKPRR [SEQ ID. NO:5]) is additionally determined.

Most particularly in the methods of the present invention, the abundance of one of these proteins or amino acid sequences is compared to a reference. The relative abundance of these proteins and amino acid sequences as determined through the methods described herein are particularly suited for the prognosis or diagnosis of metastasis, more in particular of the lymph node involvement, most in particular the prognosis or diagnosis of breast cancer diagnosis. More particularly the relative abundance of these proteins and amino acid sequences compared to a reference as determined through the methods described herein, whereby the increased abundance of these proteins and amino acid sequences is at least two fold, preferably at least a 3 fold increase, is particularly suited for the prognosis or diagnosis of metastasis, more in particular of the lymph node involvement, most in particular the prognosis or diagnosis of breast cancer diagnosis.

The different aspects of the invention as set out in the claims are described more in detail below.

In one aspect the present invention relates to the in vitro use of one or more marker proteins, nucleotide sequences encoding these marker proteins or one or more reagents specifically identifying these marker proteins or nucleotide sequences, for the prediction, prognosis or diagnosis of metastasis in a patient, wherein said protein is selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088]. In particular embodiments these marker proteins are used in combination with Vascular Endothelial Growth Factor A isoform 111, a nucleotide sequence encoding Vascular Endothelial Growth Factor A isoform 111 or a reagent specifically identifying Vascular Endothelial Growth Factor A isoform 111. More particularly, the use of the amino acid sequence APMAEGGGQNHHEWKFMDVYQRSYCHPI-
ETLVDIFQEYPDEIEYIFKPSCVPLMR CGGCCNDE-
GLECVPTEESNITMQIMRIKPHQGQHI-
GEMSFLQHNKCECRCDKPRR [SEQ ID. NO:5] of Vascular Endothelial Growth Factor A isoform 111, or a nucleotide sequence encoding this sequence or a reagent specifically identifying this amino acid or nucleic acid in this context is envisaged.

In particular embodiments the methods involving the use of marker proteins describe above make use of one or more of the amino acid sequences selected from the group consisting of SEQ ID NO:1, SEQ ID. NO:2, SEQ ID. NO:3, SEQ ID. NO:4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO:14, SEQ ID NO: 15 SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 and SEQ ID NO: 24.

The marker proteins of the present invention are of particular use for the prediction, prognosis or diagnosis of metastasis in a patient where the metastasis is lymph node metastasis. More particularly, the patient is a cancer patient, more particularly, in a breast cancer patient.

A further aspect of the present invention relates to in vitro methods for the prediction of metastasis in a patient, comprising the use of one or more of the marker proteins described above, nucleotide sequences encoding these proteins or reagents specifically identifying one or more of these marker proteins or nucleotide sequences.

In specific embodiments, these methods comprise the steps of (1) extracting one or more of these marker proteins from a biological sample isolated from the patient and (2) determining relative abundance of these marker proteins in the extract so obtained; wherein abundance of the one or more marker proteins is indicative of metastasis. In further specific embodiments, these methods make use of a reagent specifically identifying these one or more marker proteins, such as an antibody.

Further specific embodiments of the methods according to this aspect of the invention comprise the steps of (1) extracting proteins from a biological sample isolated from the patient, (2) performing protein chip retention chromatography coupled to mass spectrometry, (3) analysing the data obtained, and comparing these data with the protein expression profile given in Table 2.

Further specific embodiments of the methods of the invention comprise in vitro methods for the prediction of metastasis in a patient, comprising the steps of:
(i) extracting proteins from a biological sample isolated from the patient;
(ii) determining mass and abundance of one or more marker proteins in the extract so obtained;
(iii) comparing the abundance of the one or more proteins with the profile given in Table 2; whereby correspondence of the abundance of the one or more marker proteins in the extract to that given in Table 2 is indicative of lymph node metastasis.

In specific embodiments of these methods step (ii) comprises performing protein chip retention chromatography coupled to mass spectrometry.

In further specific embodiments one or more of the marker proteins is selected from a group consisting of the proteins depicted in Table 2, more particularly, one or more of the marker proteins is selected from a group consisting of proteins having a mass of 2,290 (9), 2,453 (11), 2,478 (12), 7,567 (15), 11,299 (19), 11,477 (20), 15,110 (28), and 15,249 (29) m/z.

In particular embodiments the methods described above comprise determining the abundance of the one or more marker proteins in a biological sample isolated from the patient and comparing the abundance to the abundance of the one or more proteins in a reference sample or as depicted in a reference expression profile. More particularly, the abundance of the one or more marker proteins in the patient is compared to the abundance of the protein(s) in a reference sample or reference expression profile of a patient not having metastasis wherein an increase of abundance compared to the reference sample or reference expression profile is indicative of metastasis. In more particular embodiments, the increase indicative of metastasis is at least a two fold increase.

In particular embodiments of the methods described above, the biological sample is a sample from tissue selected from the group consisting of tumour tissue, tissue from an organ including blood, or other body fluids. More particularly, the biological sample is a sample of tumour tissue.

The methods described above are of particular for the diagnosis and/or prediction of metastasis in a cancer patient, more particularly for the diagnosis and/or prediction of lymph node metastasis, most particularly for the diagnosis and/or prediction of metastasis in breast cancer. Most particularly, the methods for the diagnosis and/or prediction of metastasis in breast cancer described herein involve determining the abundance of marker proteins in breast tumour tissue.

In particular embodiments, the methods of the invention for or the diagnosis and/or prediction of metastasis further comprise determining the expression of an oncogene in a biological sample isolated from the patient.

A further aspect of the invention relates to metastasis marker proteins or combinations thereof which are breast tumour proteins for use in the prediction, prognosis or diagnosis of metastasis. In particular embodiments the one or more marker proteins are selected from the group consisting of proteins with a mass of about 2,290, about 2,453, about 2,478, about 7,567, about 11,299, about 11,477, 15,110, and about 15,249 m/z. In further embodiments the one or more proteins are selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088]. The invention further relates to nucleotide sequences encoding these proteins or reagents specifically identifying these proteins or nucleotide sequences for use in the prediction, prognosis or diagnosis of metastasis.

A further aspect of the invention relates to the use of one or more marker proteins, nucleotide sequences encoding these proteins or one or more reagents specifically identifying these marker proteins or nucleotide sequences in the manufacture of a diagnostic tool for the prediction, prognosis or diagnosis of lymph node metastasis, wherein said protein is selected from the group consisting of Hemoglobin Chain alpha; Eosinophil peroxidase; Histone H4; 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088].

Yet a further aspect of the invention relates to diagnostic kits comprising two or more reagents specifically identifying a marker protein selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088] or specifically identifying a nucleotide sequence encoding these proteins. In particular embodiments, the diagnostic kits of the invention further comprise a reagent specifically identifying Vascular Endothelial Growth Factor A isoform 111.

A further aspect of the invention provides reference expression profiles representing the abundance of one or more marker proteins in a biological sample from a patient diagnosed with metastasis and/or the abundance of one or more proteins in a biological sample from a patient diagnosed not to have metastasis. In particular embodiments, the reference expression profile represents the abundance of one or more proteins selected from the group consisting of proteins characterized as having a molecular mass of about 2,290, about 2,453, about 2,478, about 7,567, about 11,299, about 11,477, 15,110, and about 15,249 m/z; In further particular embodiments, the one or more marker proteins is selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088].

In further particular embodiments, the reference expression profile further represents the abundance of Vascular Endothelial Growth Factor A isoform 111 in a reference biological sample from a patient diagnosed with metastasis and/or the abundance of one or more proteins in a reference biological sample from a patient diagnosed not to have metastasis.

In yet a further aspect the invention relates to the use of one or more reagents specifically inhibiting one or more marker proteins or nucleotide sequences encoding these marker proteins for the manufacture of a medicament for the prevention or treatment of lymph node metastasis in a patient, wherein said protein is selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088].

Yet a further aspect of the invention relates to methods of diagnosing metastasis in a patient comprising:
 (a) labelling a reagent specifically identifying a protein selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088];
 (b) administering the labelled reagent to the patient; and
 (c) detecting the localization of the labelled reagent in the patient, wherein the aberrant localization or concentration of the reagent is indicative of metastasis in said patient.

In particular embodiments, these methods are use in the diagnosis of lymph node metastasis.

Yet a further aspect of the invention relates to methods of treating metastasis in a patient, which comprise administering to the patient one or more compounds that inhibit one or more proteins selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088].

DESCRIPTION OF THE FIGURE

FIG. 1: An example of two small proteins that show significantly higher expression in node positive breast tumours, compared to node negative breast tumours.

DETAILED DESCRIPTION OF THE INVENTION

The present invention is based on the observation that the protein expression pattern of the tissue of a cancer patient, more particularly of a tumour tissue of the patient, is indicative of whether or not the patient has or will develop lymph node metastasis.

The present invention relates to the prediction of lymph node involvement in patients with cancer based on protein expression profiles. A particular embodiment of the invention relates to axillary lymph node involvement prediction in patients with breast cancer from protein expression profiles, more in particular of primary breast tumour tissue.

The term "cancer" as used herein generally refers to any type of cancer which is known to potentially involve lymph node metastasis, such as, but not limited to breast cancer, lung cancer, prostate cancer etc.

The term "metastasis" as used herein refers to the spread of cancer cells from one organ or part to another non-adjacent organ or part.

The term "biological sample" as used herein refers to a tissue sample including a tumour sample or a body fluid sample. The term "body fluid" refers to all fluids that are present in the body including but not limited to blood, plasma, serum, synovial fluid, lymph, urine, saliva or cerebrospinal fluid. The biological sample may also be obtained by subjecting it to a pretreatment if necessary, for example, by homogenizing or extracting. Such a pretreatment may be selected appropriately by those skilled in the art depending on the biological sample to be subjected.

The term "expression profile" as used herein refers to a representation (either graphically or in the form of data) of the expression of one or more marker proteins or amino acid sequences in one or more tissues. This includes but is not limited to a differential expression pattern, whereby expression of the proteins in two different tissues is provided. In the context of the present invention, a differential expression profile refers to the representation of the expression of said protein in a tissue of a patient with lymph node metastasis and in the same tissue of a patient without lymph node metastasis, as determined by the same or a comparable method. A reference expression profile as used herein refers to the representation of the expression of one or more marker proteins (or amino acid sequences) in one or more reference tissues. Typically, in the present invention the reference tissues are one or more samples of cancer tissue of a patient diagnosed with metastasis and/or one or more samples of cancer tissue of a patient diagnosed without metastasis.

The term "reagent specifically identifying" referring a protein, amino acid sequence or nucleotide sequence as used herein refers to any compound which specifically binds a proteins and/or amino acid sequence or nucleotide sequence described herein and can be used for the specific identification thereof. For the identification of proteins and/or amino acid sequences, such reagents typically include binding agents such as antibodies (including derivatives thereof), and, depending on the nature of the protein to be detected, reagents specifically binding to a protein may include substrates, specifically binding enzymes, receptors, ligands, etc. The term 'antibody' as used herein generally refers to a polypeptide that displays one or more binding properties for an antigen and includes immunoglobulins, functional fragments and derivatives of immunolgobulins, such as but not limited to Fc, Fab, Fab', F(ab')2, scFv, Fv, dimers, minibodies, diabodies, domains of heavy and/or light chains of the variable riogen (such as dAb, Fd, Vk, Vh, VHH etc.) or other fragments which can be synthesized by recombinant techniques or can be chemically synthesized.

In the context of specific nucleotide sequence detection such a reagent specifically identifying the target is typically a probe, i.e. a nucleotide sequence which is at least partially complementary to the sequence of interest and capable of specifically hybridizing to the sequence of interest.

The present invention relates to the identification of proteins which are believed to play a role in metastasis of cancer. It is accordingly envisaged that these proteins can be used as marker proteins for the prediction, prognosis or diagnosis of lymph node metastasis and that strategies involving reducing the expression of these proteins can be used in the treatment of metastasis.

The present invention relates to marker proteins identified herein, either by their mass (and relative abundance) and/or their amino acid or nucleic acid sequences or parts thereof, and their use in the diagnosis or prediction of metastasis in patients, more particularly in patients with cancer, most particularly for the diagnosis and/or prediction of lymph node metastasis in breast cancer patients. The present invention also relates to the use of differential protein expression profiles, such as that provided in Table 2 for the prediction of lymph node metastasis in breast cancer patients.

In particular embodiments the marker proteins envisaged for use in the context of the present invention are proteins (or protein fractions) which are characterized by their mass (and relative abundance) such as provided in Table 2 herein. These are of particular interest where the material and/or time constraints do not allow sequence identification of proteins in a patient sample. Most particularly marker proteins according to this aspect of the present invention include the proteins with numbers 9, 11, 12, 15, 19, 20, 28, and 29 of Table 2, even more particularly, the proteins identified with numbers 9, 11, and 12. Accordingly, in particular embodiments, the metastasis marker protein according to the present invention is a protein having a mass of about 2,290 (9), 2,453 (11), 2,478 (12), 7,567 (15), 11,299 (19), 11,477 (20), 15,110 (28), and 15,249 (29) (m/z), with an error margin of 3 kDa.

In addition the present invention envisages the use of the expression profile of one or more of these proteins in a tissue of metastatic and/or non-metastatic patients for use in the prediction and prognosis of metastasis.

The metastasis marker proteins of the present invention can be used as an indicator of metastasis either alone or in combination. Although these marker proteins make it possible to detect metastasis when used alone, the accuracy of diagnosis and/or prognosis is increased when two or more of these markers are used. Furthermore, the metastasis marker proteins according to the present invention may also be used in combination with a known cancer and/or metastasis marker, such as an oncogene.

Accordingly, the present invention provides expression profiles such as those provided in Table 2 (or other representations of the data provided therein), more particularly expression profiles of one or more of the marker proteins with numbers 9, 11, 12, 15, 19, 20, 28, and 29 of Table 2, most particularly expression profiles of the proteins with numbers 9, 11, and 12 of Table 2. In particular embodiments, differential expression patterns of these proteins are provided, whereby the expression level of the protein is provided in a tissue of a patient with metastasis and in a tissue of a patient without metastasis. In particular embodiments the expression profile represents the expression of one or more of these proteins in a tumour tissue of a patient with lymph node metastasis and in a tissue of a patient without lymph node metastasis. The expression level of the one or more proteins typically represents average expression of the protein in two or more, more particularly four or more patients. Expression of a protein as measured in a protein extract is typically represented as the concentration of the protein, whereby the value will be determined by the measurement method. In particular embodiments the expression level is represented as abundance of the protein in a sample as determined by mass spectrometry. Suitable devices for performing mass spectrometry include, but are not limited to, a quadrupole mass spectrometer, a time-of-flight mass spectrometer or a protein chip systems (such as reverse-phase protein chips, metal-ion-fixed protein chips, and cation-exchange protein chips). Accordingly, the present invention furthermore relates to methods for the prediction of lymph node metastasis in cancer patients by measuring the amount of one or more of the marker proteins identified in Table 2 herein.

In further particular embodiments of the invention, metastasis marker proteins are provided which are identified by additional parameters, such as but not limited to, their amino acid sequence. For the identification of the proteins listed in Table 2 or other protein fractions which, based on their differential expression can be used as metastasis markers, standard methods and protocols known in the art can be used, one of these is more in detailed described in the examples of this invention. Upon Identification of the proteins and the amino acid sequence, by methods known in the art, including but not limited to amino acid sequencing, it is known by a person skilled in the art to use these proteins or amino acid sequences to derive specific reagents such as antibodies against these proteins or amino acid sequences. Measuring, of the amount of the identified proteins from Table 2, may be performed on protein extracts from breast tumour tissue or may be performed on blood samples. In particular embodiments, measuring may be performed by using mass spectrometry or by other methods known in the art such as antibody detection of proteins (ELISA), making use of said specifically derived antibodies.

In particular embodiments, however, the present invention provides methods for the prediction of the presence of metastasis in cancer, more in particular metastasis in lymph nodes in patients with cancer, most particularly metastasis in axillary lymph nodes in patients with breast cancer, which involve obtaining an expression profile of one or more proteins as identified by their mass such as in Table 2. Said methods may for instance comprise the steps of extracting proteins from a tumour tissue, more particularly breast tumour tissue isolated from the patient, performing Protein-Chip retention chromatography coupled to mass spectrometry, analysing the data obtained and comparing the data of one or more proteins so obtained with the differential protein expression profile given in Table 2 hereof. If 75%, more in particular 80% or 85%, yet more in particular 90% or 95% of the profile obtained with the (breast) tumour tissue fits within the lymph node negative profile (for example in the case of 90% meaning that 90% of the abundance of the proteins measured falls within the abundances and their standard deviation given in Table 2 for the lymph node negative profile), it is predicted that the lymph nodes of the patient under investigation are not metastasised. If 75%, more in particular 80% or 85%, yet more in particular 90% or 95% of the profile obtained with the breast tumour tissue fits within the lymph node positive profile, it is predicted that the lymph nodes of the patient under investigation are metastasised.

In particular embodiments, methods according to this aspect of the invention are performed using a group of marker proteins selected from the proteins with numbers 9, 11, 12, 15, 19, 20, 28, and 29 from Table 2, more particularly selected from the proteins with numbers 9, 11, 12, 15, 28 and 29 from Table 2. In more particular embodiments, the methods are performed using at least 3 proteins selected from the group of proteins with numbers 9, 11, 12, 15, 19, 20, 28, and 29 from Table 2, or using at least 3 proteins selected from the group of proteins with numbers 9, 11, 12, 15, 28 and 29 from Table 2. In further particular embodiments the methods involve determining whether the expression profile of one or more of the proteins corresponding to numbers 9, 11, 12, 15, 28 and 29 as in Table 2 in the (tumour) tissue of the patient represents an at least twofold, preferably three-fold increase compared to the level of the corresponding protein in Table 2 in lymph node negative samples.

Most particularly, the methods involve using the proteins with numbers 9, 11 and 12. In a particular embodiment, said method further comprises (a selection of) each of the steps as described in the examples under materials and methods, such as but not limited to the use of cation exchange, anion exchange and copper-loaded metal affinity protein chip arrays.

A further aspect of the present invention provides metastasis marker proteins which have been identified to correspond to Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088]. Particular embodiments of the invention relate to the marker proteins Hemoglobin Chain alpha, Eosinophil peroxidase, Histone H4, and 60S ribosomal protein L32. The invention further relates to the use of these marker proteins in methods for the prediction and/or prognosis of metastasis in cancer patients. More particularly these methods are based on determining the abundance of expression of one or more of these marker proteins in a biological sample or tissue of a patient. The present inventors have found that, as these marker proteins show differential abundance in biological samples of patients with metastasis compared to samples of patients without metastasis, these proteins can be used as metastatic marker proteins. Particular embodiments of the methods according to this aspect of the invention are based on determining, in a sample of a patient, the abundance of one or more marker proteins selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, and Albumin. Further particular embodiments of the methods described herein involve the determination of the abundance of two or more of these proteins, or 3 or more or 4, 5, 6, 7, 8, 9, 10, 11, 12, 13, 14, 15, 16, 17, 18, 19, 20, 21, 22, or all 23 of these proteins. Further particular embodiments of the methods of the present invention involve the use of the marker proteins Hemoglobin Chain alpha, Eosinophil peroxidase, Histone H4, and 60S ribosomal protein L32.

In particular embodiments, the methods of the invention further comprise, in addition to the use of one or more of the markers described above, the use of Vascular Endothelial Growth Factor A isoform 111 as a metastatic marker, more particularly involve determining the expression of Vascular Endothelial Growth Factor A isoform 111 in a biological sample of a patient.

Methods for determining abundance of a marker protein suitable for use in the context of in vitro/ex vivo methods of the present invention are known in the art. Most particularly, these include detection at the protein level. In particular embodiments the methods involve detection at the protein level, including, but not limited to
  chromatographic methods such as but not limited to (HP)LC, FPLC, TLC, etc.
  electrophoretic methods such as 1D or 2D protein electrophoresis
  immunological assays such as but not limited to enzyme-linked immunosorbent assays (ELISA), immunoblotting, immunospotting (such as line immunoassays or LIA), radioimmunoassays, fluid or gel precipitation reactions, immunodiffusion (single or double), agglutination assays, immunoelectrophoresis, time-resolved immunofluorometric assay (TRIFMA), Western blots, liposome immunoassays, complement-fixation assays, immunoradiometric assays, fluorescent immunoassays, protein A immunoassays or immunoPCR.

The detection of proteins in a biological sample may, in some embodiments require the pretreatment of the biological sample. Suitable pre-treatment steps include but are not limited to filtration, (partial) purification, concentration and more particularly protein extraction, Additionally or alternatively abundance of a marker protein proteins and/or amino acid sequence of the present invention in a sample can in some situations be determined based on expression at the RNA level. Expression levels of mRNA can be quantified by a number of methods. Traditional methods include but are not limited to Northern blot analysis, real-time PCR or kinetic RT-PCR. Similarly to the protein detection methods described above, mRNA detection methods may require the pre-treatment of a biological sample using methods such as, but not limited to filtration, (partial) purification, concentration and more particularly, RNA extraction. Depending on the sample, abundance of mRNA is representative of the abundance of the protein it encodes. Accordingly, while when referring to the methods of the present invention reference will typically be made to the detection at the protein level, it will be understood to the skilled person that, in particular embodiments, similar results can be obtained using detection at the RNA level.

In particular embodiments, the methods of the present invention involve the detection of one or more marker proteins, amino acid sequences and/or nucleic acid sequences using reagents capable of specifically identifying these marker proteins, amino acid sequence and/or amino acid sequences. Accordingly, in particular embodiments, the present invention envisages the use of reagents capable of specifically identifying the proteins and/or amino acid sequences or the nucleic acid sequences encoding these proteins and/or amino acid sequences in methods for prediction and/or prognosis of metastasis (more particularly lymph node metastasis) in cancer patients.

In particular embodiments the invention provides the use of one or more reagents specifically identifying a protein selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088].

Depending on the technology used, the reagents capable of specifically identifying the proteins, amino acids sequences and/or nucleotide sequences of the invention are typically labeled, e.g. with chromophoric or magnetic or radioactive labels, so as to allow detection, or are used in combination with other reagents which are labeled or which allow detection of the specific binding of the reagent with the marker protein, amino acid sequence or nucleotide sequence of interest.

The methods which allow the quantitative detection of a protein, amino acid sequence or nucleic acid sequence in a sample such as those provided as non-limiting examples above allow the determination of the relative abundance of the protein of interest in a sample and/or allow absolute quantification of the protein in the sample.

In particular embodiments, the methods for the prediction and/or prognosis of metastasis in cancer patients, comprise, in addition to a step involving the determination of the abundance of a marker protein (or of an amino acid sequence thereof or of a nucleotide sequence encoding such protein or amino acid sequence) in a sample of a patient, the step of comparing the abundance of that marker protein in the sample so determined to a reference. Such a reference may be obtained by determining the abundance of the protein of interest in one or more reference samples (simultaneously or at a different time). Such a reference may be an expression profile of the protein of interest which has been previously determined. The marker proteins of the present invention are proteins which have been determined by the present inventors to be up-regulated in biological samples from cancer patients with metastasis compared to biological samples from cancer patients not showing metastasis. Determining whether or not the abundance of the protein of interest in a sample corresponds to an "up-regulated" or a "non-up-regulated" profile of the protein, is typically performed by comparing the abundance of the protein determined in the sample with the abundance as determined (preferably using the same method) in a biological sample (or an average of several of such samples) from a cancer patient with metastasis and/or in a biological sample (or an average of such samples) from a cancer patient not showing metastasis. Accordingly, in particular embodiments of methods of the present invention the step of comparing the abundance of the (one or more) marker protein(s) to a reference comprises determining whether or not the abundance of the protein(s) is (at least) similar to (or higher than) that determined in a biological sample of a cancer patient diagnosed with metastasis (reference sample), whereby a positive outcome is indicative of metastasis in the patient.

The marker proteins of the present invention have been found to be present at least twice as abundantly in biological samples from cancer patients with metastasis compared to their abundance in biological samples from cancer patients without metastasis. Accordingly, in particular embodiments, the methods of the present invention comprise the step of determining whether or not the abundance of the (one or more) marker protein(s) as determined in the sample is at least twice as high, more particularly at least a threefold of the abundance of the corresponding (one or more) marker protein(s) in a sample from a cancer patient diagnosed to be without metastasis (reference sample), whereby a positive outcome is indicative of metastasis in the patient. It will be understood to the skilled person that the reference can represent an average of multiple reference samples or can represent a value of pooled reference samples.

In further particular embodiments of the invention methods of prediction and prognosis of metastasis in a (cancer) patient are provided which comprise a step of determining the abundance of one or more marker proteins in a biological sample of the patient and the step of comparing the abundance so determined with two references, i.e. the abundance of the one or more marker proteins in a sample from a cancer patient with metastasis and the abundance of the one or more marker proteins in a sample from a (cancer) patient without metastasis.

Of course it will be understood by the skilled person that, for a given detection method, absolute values (or ranges of values) can be determined corresponding to the level of the marker protein typically measured in a sample of a (cancer) patient with or without metastasis, such that, once these values are known, "comparison" as such is no longer necessary but comes down to determining whether or not the abundance determined for the marker protein in the sample corresponds to one or the other predetermined value.

As indicated above, the references of use in the methods of the present invention may take the form of actual samples for which the abundance of the protein are determined together with the test sample. Alternatively, the reference takes the form of predetermined expression pattern or profile of one or more marker proteins.

Accordingly, the present invention further relates to reference expression profiles of one ore more of the marker proteins of the invention and the use thereof in the diagnosis and prognosis of metastasis. As detailed above, such a reference expression profile can correspond to a representation of the abundance of a set of proteins identified only by their mass. For instance, the abundance of one or more proteins, more particularly two or more marker proteins e.g. within a molecular mass range is provided for a positive (with metastasis) and negative (without metastasis) reference. Typically, the molecular weight range is between 500 and 100,000 Dalton, more particularly between 1000 and 50,000 Dalton, even more particularly between 1100 and 45,000 Dalton, such as between 1200 and 42,000 Dalton. Further particular embodiments comprise ranges of proteins between 1200 and 5000 Dalton. Such expression profiles typically comprise between 1 and 20 marker proteins, more particularly between 2 and 10 marker proteins, most particularly about 5 marker proteins of which the abundance of expression is indicative for metastasis.

Additionally or alternatively, the reference expression profiles envisaged herein can refer to specifically identified sequences or fragments thereof. More particularly, the present invention relates to reference expression profiles of one or more marker proteins, wherein the marker proteins comprise proteins selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088] and the use thereof in the prediction or diagnosis of metastasis, more particularly lymph node metastasis in a cancer patient. Such reference expression profiles may include the expression of one or more, such as two or more of these proteins, or 3 or more or 4, 5, 6, 7, 8, 9, 10, 11, 12, 13, 14, 15, 16, 17, 18, 19, 20, 21, 22, or all 23 of these marker proteins in a biological sample from a (cancer) patient with metastasis and/or in a biological sample from a (cancer) patient without metastasis. In particular embodiments reference expression profiles are provided which indicate (either graphically or in numerical values) the abundance of one or more of these marker proteins in a tumour tissue sample from a cancer patient with metastasis and/or in a tumour tissue sample from a cancer patient without metastasis. Particular embodiments of the invention relate to reference expression profiles of these proteins in breast tumour tissue samples of breast cancer patients with and without metastasis.

The method of detection used (which is typically the same for the reference and for the sample of interest) will determine the nature of the value representing the abundance of the protein. As indicated above, these values may be presented in different ways, including but not limited to numerical values or graphs, may be on paper or in electronic form or may be integrated in a computer program of a detection device.

As detailed above, the invention envisages reference expression profiles comprising data on the abundance of one or more of the marker proteins disclosed herein. Typically, more than one marker will be used and the reliability of the methods of prediction and diagnosis increases with the number of markers used. It is envisaged that where more than one marker is used, the higher the level of correspondence between the values for the different marker proteins in the sample compared to that of a reference sample or reference expression profile, the more reliable the methods of prediction will be. More particularly, if 75%, more in particular 80% or 85%, yet more in particular 90% or 95% of the profile obtained with the tissue from the patient fits within the metastasis negative reference sample values or reference expression profile (for example in the case of 90% meaning that 90% of the abundance of the marker proteins measured falls within the abundances of the reference and their standard deviation), it is predicted that the patient under investigation does not have metastasis. If 75%, more in particular 80% or 85%, yet more in particular 90% or 95% of the profile obtained for the tissue sample of the patient fits within the metastasis positive reference sample values or reference profile, it is predicted that the patient under investigation does have metastasis. More particularly, where the method involves determining lymph node metastasis in breast cancer patients, If 75%, more in particular 80% or 85%, yet more in particular 90% or 95% of the profile obtained with the (breast)

tumour tissue of the patient fits within the lymph node negative profile (for example in the case of 90% meaning that 90% of the abundance of the proteins measured falls within the abundances and their standard deviation), it is predicted that the lymph nodes of the patient under investigation are not metastasised. If 75%, more in particular 80% or 85%, yet more in particular 90% or 95% of the profile obtained with the breast tumour tissue of the patient fits within the lymph node positive profile, it is predicted that the lymph nodes of the patient under investigation are metastasised.

In a further aspect of the present invention diagnostic kits are provided for use in the prediction or diagnosis of metastasis. In particular embodiments, the kits envisaged in the context of the present invention comprise one or more reference expression profiles such as described above.

In other embodiments, the diagnostic kits of the present invention comprise one or more, typically two or more reagents specifically identifying a marker protein according to the invention. Most particularly, a diagnostic kit may comprise one or more, typically two or more reagents specifically identifying a marker protein selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi:119602615] and MSTP132 [gi:33338088]. Further particular embodiments of the diagnostic kits of the invention comprise reagents specifically detecting 3 or more or 4, 5, 6, 7, 8, 9, 10, 11, 12, 13, 14, 15, 16, 17, 18, 19, 20, 21, 22, or all 23 of these marker proteins. In particular embodiments, the diagnostic kits contain, in addition to one or more of the reagents recited above, a reagent specifically identifying Vascular Endothelial Growth Factor A isoform 111. Such reagents are typically antibodies or derivatives thereof but may be any binding agent which allows specific detection of a marker protein. Typically, the reagents are suitable for use in an immunologic assay and are labeled or are suitable for use in combination with secondary labeled reagents. Where the methods of the present invention comprise detection of mRNA, the corresponding diagnostic kits envisaged are kits comprising suitable probes for the specific detection of protein expression at the mRNA level.

In further particular embodiments, diagnostic kits are provided which are integrated (optionally disposable) devices which optionally contain, in addition to the marker-specific reagents, one or more additional reagents required for carrying out the detection of the abundance of one or more marker proteins. The specific reagents may also be provided on a chip.

In further particular embodiments, diagnostic kits are provided which contain a combination of one or more marker-specific reagents and one or more reference samples or expression profiles, e.g. a combination of one or more marker-specific reagents and a computer program which allows evaluation of the values detected.

The methods and tools of the present invention are envisaged to be of use in the prediction or diagnosis of metastasis in a patient. Though particular embodiments of the present invention relate to methods carried out on humans, it is envisaged that these methods may also be of use in other mammals.

Particularly, the methods and tools of the present invention are envisaged for use in the prediction, prognosis or diagnosis of a patient with cancer. More particularly, the methods and tools provided are of use in determining whether a patient has or is likely to develop metastasis, most particularly lymph node metastasis, i.e. involvement of the lymph nodes in the spreading of cancer. The methods of the invention (and the tools provided for performing these methods) are particularly suited for the diagnosis and/or prognosis of breast cancer. However, it is envisaged that the markers of the present invention are equally of use in the diagnosis and/or prognosis of other forms of (potentially) metastasizing cancers such as prostate cancer, lung cancer, liver cancer, pancreas cancer etc.

The methods of the invention make it possible to determine whether or not a patient suffers or is likely to suffer from metastasis, based on the determination of the abundance of expression of one or more marker proteins in a biological sample of the patient. Typically, the biological sample is a sample of tumour tissue, isolated from the patient. However, it is envisaged that other biological samples are also suitable, such as e.g. blood, lymph fluid or other tissues.

In particular embodiments, the step of detecting the abundance of one or more marker proteins in the methods of the invention is carried out in vitro or ex vivo, i.e. on a sample isolated from the body of the patient. However, in alternative embodiments the methods of the step of determining the abundance of one or more marker proteins may be carried out in the body, e.g. by administering a labeled reagent capable of specifically detecting a marker according to the invention and detecting the labeled reagent in the body using e.g. nmr spectroscopy or isotope detection. In these embodiments, detection of increased abundance (e.g. compared to what is expected in healthy subjects) of one or more marker proteins of the invention and/or aberrant localization of one or more marker proteins of the invention is indicative for the presence of metastasis in the patient. For these applications the reagent specifically identifying a marker protein is necessarily a reagent which is tolerated by the human or animal body, such as, but not limited to a human or humanized antibody (where the patient is a human).

The methods of the present invention allow the diagnosis and/or prognosis of metastasis without the need for invasive surgery. Typically, in order to determine whether or not there is metastasis of cancer in a patient, sentinel lymph node biopsy or a lymph node dissection is performed. The methods of the present invention make it possible to determine metastasis without these procedures The methods of the present invention are particularly suitable for patients in which sentinel lymph node biopsy or lymph node dissection is difficult or contra-indicated. Additionally, the present invention provide methods for diagnosis of metastasis in a patient in which in a first step one or more marker proteins are determined in a biological tissue of the patient and, depending on the outcome of this determination, the step of lymph node biopsy or dissection is performed.

It is known in the art that it is of interest to determine whether or not a patient has or is likely to develop metastasis in order to select the optimal method of treatment. The methods of diagnosis and/or prognosis of the present invention allow the selection of a more appropriate treatment. Accordingly, in a further aspect, the present invention provide methods for treating a patient which comprise (a) determining whether or not the patient has or is likely to develop metastasis and (b) selecting the appropriate medication or therapeutic regimen accordingly.

According to yet a further aspect of the present invention proteins are provided which, based on their excessive abundance in samples of patients with metastasis, are believed to be involved in the process of metastasis. Accordingly, the invention provides methods for reducing or treating metastasis, which involve administering an agent which reduces the production of one or more of the marker proteins of the present invention. More particularly, the methods of treatment or prevention of metastasis of the present invention involve, administering, to a patient diagnosed with or at risk of metastasis, one or more agents capable of reducing the expression of one or more marker proteins selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta, Albumin, XP_001717485 [gi:169170953], LOC286076 [gi: 119602615] and MSTP132 [gi:33338088], more particularly selected from the group consisting of Hemoglobin Chain alpha, Eosinophil peroxidase, Histone H4, 60S ribosomal protein L32, Hemopexin, Protein DJ-1, Transgelin, Apolipoprotein A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta and Albumin. The invention further provides such agents for use in the treatment and prevention of metastasis, more particularly lymph node metastasis, most particularly for use in the treatment of breast cancer metastasis. Suitable dosages correspond to those which ensure that the level or marker protein in a biological sample of the patient is reduced to a level characteristic for the absence of metastasis and can be determined by the person skilled in the art.

EXAMPLES

Example 1

Determine of Differentially Expressed Protein Profiles in Lymph Node Positive Vs Lymph Node Negative Breast Cancers Because lymph node involvement is often the earliest sign of tumour progression, insights into the underlying molecular mechanisms are essential in order to be able to predict lymph node involvement from protein expression profiles, more in particular of primary breast tumour tissue. A pilot proteomic study in 8 patients with breast cancer was performed, investigating the differences in protein expression profiles between lymph node negative and lymph node positive breast cancers using SELDI-TOF MS. Representative biopsies were selected taking various clinicopathological and biological parameters into account.

Surface Enhanced Laser Desorption/Ionization Time-of-flight Mass Spectrometry (SELDI-TOF MS) is a valuable method for the analysis of differential protein expression in tissue extracts and body fluids (Bischoff R. et al. 2004 *J. Chromatogr. B Analyt. Technol. Biomed. Life Sci.* 803:27-40). It combines two powerful techniques: chromatography and mass spectrometry. The end result of a SELDI-TOF MS analysis is a list of the molecular weights of proteins whose relative abundance differs significantly between two groups of samples (Issaq H. J. et al. 2002 *Biochem. Biophys. Res. Commun.* 292:587-592). This technology allows sensitive and high-throughput protein profiling of complex biological specimens (Landuyt B. et al. 2004 *Amino. Acids* 27:335-337; Semmes O. J. et al. 2005 *Clin. Chem.* 51:102-112; Shiwa M. et al. 2003 *Biochem. Biophys. Res. Commun.* 309:18-25).

Using SELDI-TOF MS, we found a total of 42 proteins displaying significant differential expression (p<0.05) in breast cancers with and without lymph node involvement.

Materials and Methods

Material: Eight primary breast cancers were selected from the tumour bank (−80° C.) of the University Hospital Gasthuisberg. Patients were selected very carefully from a large tissue bank in order to get 2 homogeneous groups, differing only in lymph node involvement. Tissue samples were stained with hematoxylin and eosin and evaluated by a pathologist. All tissues were histopathologically classified as poorly differentiated invasive ductal carcinoma and contained more than 75% tumour cells. All patients underwent an axillary lymph node dissection: 4 patients were lymph node negative, 4 patients were lymph node positive.

All patients except 1 were postmenopausal and mean patient age was 64 years (range, 43-71 years) with a mean tumour size of 2.5 cm (range 1.6-4 cm). The estrogen receptor (ER) was evaluated on the primary tumour specimen by standard immunohistochemistry and was positive in all patients. Additional clinicopathologic characteristics are listed in Table 1.

TABLE 1

Clinicopathologic characteristics of selected samples.

| | Node negative | Node positive |
|---|---|---|
| Mean age (years) | 67.25 | 60.75 |
| Mean NPI | 4.475 | 6.29 |
| Mean Tumour diameter (cm) | 2.375 | 2.7 |
| Mean metastatic lymph nodes | 0 | 3.75 |

NPI: Nothingham Prognostic Index (Elston C. W. Aust N Z J Surg. 1984 54(1): 11-15; Todd J. H. Br J Cancer. 1987 October; 56(4): 489-92.)

Protein extraction: Protein extracts were prepared by crushing 10 mg of breast tumour tissue in liquid nitrogen with a mortar and pestle. The pulverised tissue was dissovolved in 1 ml of protein extraction buffer (9M Urea, 1% CHAPS and 1% Protease Inhibitor Cocktail) by brief homogenisation with a tissue homogenisator. The extracts were centrifuged for 5 minutes at 10,000 g (4° C.) and the supernatant was aliquoted and frozen at −80° C. Total protein concentrations were measured with a Bradford protein assay (Bio-Rad, Hercules, Calif.).

ProteinChip retention chromatography: All experiments were performed in duplicate. The protein extracts were normalized to a final concentration of 0.5 µg/µl in extraction buffer. These extracts were diluted 20 fold in the different ProteinChip binding buffers (0.1M Ammonium Acetate pH 4 for Cation Exchange arrays, 50 mM Tris-HCl pH 9 for Anion Exchange arrays, and 0.1M Sodium Phosphate/0.5M Sodium Chloride for copper-loaded metal affinity arrays).

Cation exchange, anion exchange and copper-loaded metal affinity ProteinChip arrays were mounted in a bioprocessor and every spot was rinsed two times with 100 µl of the respective binding buffer for 5 minutes a room temperature. The arrays were than loaded with 100 µl of the diluted protein extract per spot, and incubated for 45 minutes at room temperature with vigorous shaking on a Micromix 5 (DPC, Los Angeles, Calif.). After incubation, the arrays were washed three times with 100 µl of binding buffer per spot for 5 minutes at room temperature. The arrays were desalted prior to mass spectrometry (MS) by a bulk wash with ultra pure water.

Mass spectrometry: The energy absorbing matrices sinnapinic and cinnaminic acid (Ciphergen Biosystems, Fremont, Calif.; 2.5% solutions in 50% Acetonitrile/0.5% Trifluoro Acetic Acid) were added twice (0.8 µl/spot), and the arrays were dried in a dark room. The proteins bound to the retention chromatographic ProteinChip arrays were then analysed by SELDI TOF MS on a PBS II system (Ciphergen Biosystems, Fremont, Calif.). The instrument was externally calibrated with peptide and protein standards (Ciphergen Biosystems, Fremont, Calif.), according to the manufacturer's instructions, and was operated in an air conditioned room with a constant temperature of 22° C.

Data analysis: All spectra were normalised against the total ion current, and background was substracted at 8 times the expected value of the peak width. Biomarker wizard software (Ciphergen Biosystems, Fremont, Calif.) was used to calculate statistically significant differences in protein expression between the two defined sample groups (breast cancer with and without lymph node involvement). Only peaks with a minimal signal to noise ratio of 5 were retained for the first pass cluster determination, and a minimal signal to noise ratio of 3 was applied for the second pass cluster determination.

Results

A total of 42 proteins displayed significant differential expression (p<0.05) between breast cancers with lymph node involvement versus breast cancer without lymph node involvement.

The molecular weights of these proteins ranged from 1300 to 42000 Dalton. Twenty proteins were upregulated in the lymph node positive group, and 22 proteins were upregulated in the lymph node negative group. Most differences were seen on anion exchange arrays (29), followed by copper loaded metal affinity arrays (7) and cation exchange arrays (6). An example of two small proteins/peptides that were found to be significantly higher expressed in the lymph node positive group is presented in FIG. 1.

These data show that breast cancers with and without lymph node involvement express different proteins. The identification of the proteins with a differential expression profile is shown in Table 2.

Example 2

Identification of Differentially Expressed Proteins

For the identification of the proteins listed in Table 2, standard methods and protocols known in the art can be used. The different proteins can be collected individually and than sequenced with an automated amino acid sequencer.

Materials and Methods

Peptide Purification

250 µl of tissue extract was diluted with 250 µl 50 mM Tris-HCl pH 9 and loaded on an anion exchange mini spin column (Sartorius, Aubange, France) that was equilibrated with 500 µl 50 mM Tris-HCl pH 9. After binding of the peptides to the membrane, the column was washed three times with 500 µl 50 mM Tris-HCl pH 9 and the peptides were finally eluted with 500 µl 50% Acetonitrile/1% Formic Acid. The eluate was subsequently evaporated in a vacuum centrifuge and re-dissolved in 10 µl 500 mM Tris-HCl pH 9.

5 µl of this purified and concentrated fraction of anionic peptides was then loaded on an anion exchange ProteinChip array and incubated in a humid chamber for 1 hour at room temperature. Finally, the ProteinChip surface was desalted by a bulk wash with ultra pure water.

Peptide Identification 1.5 µl of a saturated solution of cinnaminic acid (Sigma-Aldrich, St-Louis, Mo.) in 50% Acetonitrile/0.5% Trifluoro Acetic Acid was applied on the ProteinChip surface and was allowed to dry to the air in a dark room before further analysis.

The ProteinChip was then mounted in a stainless steel ProteinChip-MTP adapter (Bruker Daltonics, Bremen, Germany) and was analyzed with Matrix Assisted Laser Desorption/Ionization Time-of-Flight Mass Spectrometry (MALDI TOF MS, Ultraflex II, Bruker Daltonics, Bremen, Germany). The instrument was operated in an air conditioned room with a constant temperature of 22° C. and was externally calibrated from a normal phase ProteinChip array with a standard peptide mixture (Bruker Daltonics, Bremen, Germany) to a mass accuracy of less than 20 ppm.

Peptides of interest were selected for further analysis by the use of the precursor selection window (PCIS) and post-source decay (PSD) fragments of the respective parent ions were accelerated in a LIFT electrical field, enabling $MS^2$ analysis.

The resulting $MS^2$ data were queried against the Swiss-Prot database of human proteins that was installed on an in-house Mascot server (Matrix Science, London, UK).

Results

For the identification of proteins, in particular the proteins listed in Table 2, standard methods and protocols known by a person skilled in the art can be used. Three proteins from Table 2, are identified by the methods described in this example 2:

(9) 2290 Da: EETRGVLKVFLENVIRDAVT [SEQ ID NO:1] is from Histone H4

(11) 2452 Da: NIGYGSNKKTKHMLPSGFRKF [SEQ ID. NO:2] is from 60S ribosomal protein L32, K stands for AceK meaning that this lysine residue is acetylated

(12) 2477 Da: WLPAEYEDGLSLPFGWTPSRR [SEQ ID. NO:3] is from Eosinophil peroxidase

(28) 15110 Da: VLSPADKTNVKAAWGKVGA-HAGEYGAEALERMFLSFPTTKTYFPHFDLSHG SAQVKGHGKKVADALTNAVAHVDDMP-NALSALSDLHAHKLRVDPVNFKLLS HCLLVT-LAAHLPAEFTPAVHASLDKFLASVSTVLTSKYR [SEQ ID. NO:4] is from Hemoglobin Chain alpha APMAEGGGQNHHEWKFMDVYQRSYCHPI-ETLVDIFQEYPDEIEYIFKPSCV PLMRCGGC-CNDEGLECVPTEES NITMQIMRIKPHQGQHIGEMSFLQHNKCE CRCDKPRR [SEQ ID. NO:5] is from Vascular Endothelial Growth Factor A isoform 111; N stands for carboN meaning that the aparagine residue is glycosylated.

Example 3

Two-Dimensional Gel Electrophoresis Followed by Protein Identification

Materials and Methods

All materials, reagents and software for 2 Dimensional Differential Gel Electrophoresis (2D DIGE) were purchased from GE Healthcare (London, UK).

Sample Preparation for 2D DIGE Analysis

In this study, 12 breast carcinoma tissue extracts were used, 6 lymph node metastasis positive and 6 lymph node metastasis negative control samples. 50 µg of each tissue protein extract was labeled with 200 pmol of Cy3 or Cy5 (two "forward" and two "reverse" labeled samples were prepared for the two sample groups), whereas 50 μg of pooled internal standard was labeled with 200 pmol of Cy2. The internal standard consisted of a pool of all lymph node positive and negative breast carcinoma tissue extracts. The labeling reaction was carried out for 30 min on ice and quenched with 10 mM lysine (15 min on ice). Labeled protein extracts were pooled, and sample loading buffer was added (7 M urea, 2 M thiourea, 4% w/v CHAPS, 0.5% v/v Isoelectric Phocussing (IPG) buffer, and 1.2% v/v Destreak).

2D DIGE and Gel Imaging

IPG strips (24 cm, pH 3-10) were rehydrated overnight in 450 μl of rehydration buffer (7 M urea, 2 M thiourea, 4% w/v CHAPS, 0.5% v/v IPG buffer, and 1.2% w/v Destreak. The pooled samples containing sample loading buffer were loaded onto the rehydrated strips using anodic cup loading and separated according to their isoelectric point on an Ettan IPGphor II manifold. The complete process was tracked using the Ettan IPGphor control software (version 1.01.03). The first dimension was ended when the current reached a stable phase (at ~60 kV-h).

Prior to the second dimension, the strips were equilibrated during two intervals of 15 min each in an equilibration buffer (6 M urea, 30% v/v glycerol, 2% w/v SDS, and 50 mM Tris-HCl, pH 8.8) containing 1% w/v DTT in the first step and 4% w/v iodoacetamide and 0.02% bromphenol blue in the second step. Equilibrated strips were placed on top of 12.5% SDS-polyacrylamide gel and separated on an Ettan DaltSix system, Scanning of the gels was performed using a Typhoon 9400 at 100-μm pixel size. Prior to analysis with the DeCyder™ Version 6.5 software, gel images were cropped using ImageQuant TL. Spot detection and matching was performed automatically using the "Batch Processor" module of the DeCyder Version 6.5 software followed by careful manual rematching of wrongly matched spots or unmatched spots.

Spot Picking and Protein Digestion

For spot picking, a preparative gel was run (6 times 100 μg of protein extract pooled from each lymph node positive tumour sample). The first and second dimension run was performed as described above except that CyDye labeling was omitted. Glass plates were pretreated with BindSilane, and two reference markers were applied to enable automatic picking. The gels were poststained using Deep Purple. Matching with the analytical gels was performed using the biological variation analysis module of the DeCyder Version 6.5 software. A pick list was generated and exported into the Spot Picker Version 1.20 software that controls the Ettan Spot Picker.

Spots were picked in ultrapure water, transferred to 100 μl of fixation solution (50% v/v methanol, 5% v/v acetic acid, and 45% v/v ultrapure water) and rinsed three times with ultrapure water and three times with ACN. The gels were hydrated in a 100 mM ammonium bicarbonate solution for 10 min followed by a dehydration step in 100% ACN for 10 min with vigorous vortexing. This step was repeated twice prior to dehydrating the gel pieces in a SpeedVac.

Gel pieces were rehydrated in digestion buffer (50 mM ammonium bicarbonate and 5 mM CaCl2) containing 5 ng/μl modified trypsin (Promega, Madison, Wis.) and incubated overnight at 37° C. The resulting peptides were extracted out of the gel plugs in four steps: once with 50 mM ammonium bicarbonate, twice with 50% v/v ACN and 5% v/v formic acid, and once with 95% ACN and 5% formic acid (30 min each). Supernatants of respective proteins were pooled and dried in a SpeedVac.

Protein Identification

Tryptic peptides were analyzed by nano Liquid Chromatography/tandem Mass Spectrometry (nanoLC/MS/MS) using an Ultimate3000 nanoLC system (Dionex, Amsterdam, The Netherlands) coupled to an Electrospray Ionization Quadrupole Time-Of-Flight (ESI QTOF) mass spectrometer (MicrOTOF-Q, Bruker Daltonics, Bremen, Germany). Chromatography was performed using a guard column (μ-guard column MGU-30 C18, Dionex, Amsterdam, The Netherlands) acting as a reverse phase support to trap the peptides. Prior to analysis, the dried tryptic peptides were redissolved into 5 μl of 5% v/v ACN in ultra pure water with 0.5% v/v formic acid and they were subsequently loaded on the pre-column with an isocratic flow of ultra pure water with 0.5% v/v formic acid at a flow rate of 30 μl/min. After 2 min, the column-switching valve was switched, placing the pre-column online with the analytical capillary column, a C18 of 75 μm×150 mm nano column (Pepmap, Dionex, Amsterdam, The Netherlands). Separation was conducted using a linear gradient from 95% v/v solvent A and 5% v/v solvent B to 20% v/v A and 80% v/v B in 90 min, followed by a linear gradient from 20% v/v A and 80% v/v B to 50% v/v A and 50% v/v B in 60 min (solvent A: 99.5% v/v ultrapure water/0.5% v/v formic acid; solvent B: 99.5% v/v ACN/0.5% v/v formic acid). The flow rate was set at 200 nl/min. The nanoLC system was connected in series to the electrospray interface of the ESI QTOF device. The column eluent was directed through a metal-coated fused silica tip (Picotip type FS360-75-10 D, New Objective, Woburn, Mass.). The mass spectrometer was externally calibrated with a tuning mixture (TuneMix, Agilent, Santa Clare, Calif.) to a mass accuracy of less than 2.5 ppm. The system was operated in the positive ion mode and all double, triple and quadruple charged ions (typical for peptides, background ions have generally only one charge) of sufficient parent ion intensity (threshold was set at 15 counts per second) were automatically recognized by the charge state recognition software (MicrOTOF Control version 2.4, Bruker Daltonics, Bremen, Germany), and selected for fragmentation as they eluted from the column. Argon was used as a collision gas, and the collision energy was set to 25-40 electron Volts, depending on the mass and charge state of the selected ion.

Peptides were identified by subjecting their fragmentation spectra to a batch search against the NCBI human proteome database, which was installed on an in-house Mascot server (Matrix Science, London, UK).

Results

The following proteins were found to be statistically significantly upregulated (p<0.05) in breast tumours with lymph node metastasis, compared with breast tumours without lymph node metastasis:

Hemopexin
[SEQ ID. NO: 6]
MARVLGAPVALGLWSLCWSLAIATPLPPTSAHGNVAEGETKPDPDVTE

RCSDGWSFDATTLDDNGTMLFFKGEFVWKSHKWDRELISERWKNFPSP

VDAAFRQGHNSVFLIKGDKVWVYPPEKKEKGYPKLLQDEFPGIPSPLD

AAVECHRGECQAEGVLFFQGDREWFWDLATGTMKERSWPAVGNCSSAL

RWLGRYYCFQGNQFLRFDPVRGEVPPRYPRDVRDYFMPCPGRGHGHRN

GTGHGNSTHHGPEYMRCSPHLVLSALTSDNHGATYAFSGTHYWRLDTS

RDGWHSWPIAHQWPQGPSAVDAAFSWEEKLYLVQGTQVYVFLTKGGYT

LVSGYPKRLEKEVGTPHGIILDSVDAAFICPGSSRLHIMAGRRLWWLD

LKSGAQATWTELPWPHEKVDGALCMEKSLGPNSCSANGPGLYLIHGPN

LYCYSDVEKLNAAKALPQPQNVTSLLGCTH

Protein DJ-1

[SEQ ID. NO: 7]

MASKRALVILAKGAEEMETVIPVDVMRRAGIKVTVAGLAGKDPVQCSR

DVVICPDASLEDAKKEGPYDVWLPGGNLGAQNLSESAAVKEILKEQEN

RKGLIAAICAGPTALLAHEIGFGSKVTTHPLAKDKMMNGGHYTYSENR

VEKDGLILTSRGPGTSFEFALAIVEALNGKEVAAQVKAPLVLKD

Transgelin

[SEQ ID. NO: 8]

MANKGPSYGMSREVQSKIEKKYDEELEERLVEWIIVQCGPDVGRPDRG

RLGFQVWLKNGVILSKLVNSLYPDGSKPVKVPENPPSMVFKQMEQVAQ

FLKAAEDYGVIKTDMFQTVDLFEGKDMAAVQRTLMALGSLAVTKNDGH

YRGDPNWFMKKAQEHKREFTESQLQEGKHVIGLQMGSNRGASQAGMTG

YGRPRQIIS

Apolipoprotein A-I

[SEQ ID. NO: 9]

MKAAVLTLAVLFLTGSQARHFWQQDEPPQSPWDRVKDLATVYVDVLKD

SGRDYVSQFEGSALGKQLNLKLLDNWDSVTSTFSKLREQLGPVTQEFW

DNLEKETEGLRQEMSKDLEEVKAKVQPYLDDFQKKWQEEMELYRQKVE

PLRAELQEGARQKLHELQEKLSPLGEEMRDRARAHVDALRTHLAPYSD

ELRQRLAARLEALKENGGARLAEYHAKATEHLSTLSEKAKPALEDLRQ

GLLPVLESFKVSFLSALEEYTKKLNTQ

Cellular retinoic acid-binding protein 1

[SEQ ID. NO: 10]

MPNFAGTWKMRSSENFDELLKALGVNAMLRKVAVAAASKPHVEIRQDG

DQFYIKTSTTVRTTEINFKVGEGFEEETVDGRKCRSLATWENENKIHC

TQTLLEGDGPKTYWTRELANDELILTFGADDWCTRIYVRE 60 kDa heat shock protein, mitochondrial

[SEQ ID. NO: 11]

MLRLPTVFRQMRPVSRVLAPHLTRAYAKDVKFGADARALMLQGVDLLA

DAVAVTMGPKGRTVIIEQSWGSPKVTKDGVTVAKSIDLKDKYKNIGAK

LVQDVANNTNEEAGDGTTTATVLARSIAKEGFEKISKGANPVEIRRGV

MLAVDAVIAELKKQSKPVTTPEEIAQVATISANGDKEIGNIISDAMKK

VGRKGVITVKDGKTLNDELEIIEGMKFDRGYISPYFINTSKGQKCEFQ

DAYVLLSEKKISSIQSIVPALEIANAHRKPLVIIAEDVDGEALSTLVL

NRLKVGLQVVAVKAPGFGDNRKNQLKDMAIATGGAVFGEEGLTLNLED

VQPHDLGKVGEVIVTKDDAMLLKGKGDKAQIEKRIQEIEQLDVTTSEY

EKEKLNERLAKLSDGVAVLKVGGTSDVEVNEKKDRVTDALNATRAAVE

EGIVLGGGCALLRCIALDSLTPANEDQKIGIEIIKRTLKIPAMTIAKN

AGVEGSLIVEKIMQSSSEVGYDAMAGDFVNMVEKGIIDPTKVVRTALL

DAAGVASLLTTAEVVVTEIPKEEKDPGMGAMGGMGGGMGGGMF

Heat shock 70 kDa protein

[SEQ ID. NO: 12]

MAKAAAIGIDLGTTYSCVGVFQHGKVEIIANDQGNRTTPSYVAFTDTE

RLIGDAAKNQVALNPQNTVFDAKRLIGRKFGDPVVQSDMKHWPFQVIN

DGDKPKVQVSYKGETKAFYPEEISSMVLTKMKEIAEAYLGYPVTNAVI

TVPAYFNDSQRQATKDAGVIAGLNVLRIINEPTAAAIAYGLDRTGKGE

RNVLIFDLGGGTFDVSILTIDDGIFEVKATAGDTHLGGEDFDNRLVNH

FVEEFKRKHKKDISQNKRAVRRLRTACERAKRTLSSSTQASLEIDSLF

EGIDFYTSITRARFEELCSDLFRSTLEPVEKALRDAKLDKAQIHDLVL

VGGSTRIPKVQKLLQDFFNGRDLNKSINPDEAVAYGAAVQAAILMGDK

SENVQDLLLLDVAPLSLGLETAGGVMTALIKRNSTIPTKQTQIFTTYS

DNQPGVLIQVYEGERAMTKDNNLLGRFELSGIPPAPRGVPQIEVTFDI

DANGILNVTATDKSTGKANKITITNDKGRLSKEEIERMVQEAEKYKAE

DEVQRERVSAKNALESYAFNMKSAVEDEGLKGKISEADKKKVLDKCQE

VISWLDANTLAEKDEFEHKRKELEQVCNPIISGLYQGAGGPGPGGFGA

QGPKGGSGSGPTIEEVD

Stress-70 protein, mitochondrial

[SEQ ID. NO: 13]

MISASRAAAARLVGAAASRGPTAARHQDSWNGLSHEAFRLVSRRDYAS

EAIKGAVVGIDLGTTNSCVAVMEGKQAKVLENAEGARTTPSVVAFTAD

GERLVGMPAKRQAVTNPNNTFYATKRLIGRRYDDPEVQKDIKNVPFKI

VRASNGDAWVEAHGKLYSPSQIGAFVLMKMKETAENYLGHTAKNAVIT

VPAYFNDSQRQATKDAGQISGLNVLRVINEPTAAALAYGLDKSEDKVI

AVYDLGGGTFDISILEIQKGVFEVKSTNGDTFLGGEDFDQALLRHVKE

FKRETGVDLTKDNMALQRVREAAEKAKCELSSSVQTDINLPYLTMDSS

GPKHLNMKLTRAQFEGIVTDLIRRTIAPCQKAMQDAEVSKSDIGEVIL

VGGMTRMPKVQQTVQDLFGRAPSKAVNPDEAVAIGAAIQGGVLAGDVT

DVLLLDVTPLSLGIETLGGVFTKLINRNTTIPTKKSQVFSTAADGQTQ

VEIKVCQGEREMAGDNKLLGQFTLIGIPPAPRGVPQIEVTFDIDANGI

VHVSAKDKGTGREQQIVIQSSGGLSKDDIENMVKNAEKYAEEDRRKKE

RVEAVNMAEGIIHDTETKMEEFKDQLPADECNKLKEEISKMRELLARK

DSETGENIRQAASSLQQASLKLFEMAYKKMASEREGSGSSGTGEQKED

QKEEKQ

Azurocidin

[SEQ ID. NO: 14]

MTRLTVLALLAGLLASSRAGSSPLLDIVGGRKARPRQFPFLASIQNQG

RHFCGGALIHARFVMTAASCFQSQNPGVSTWLGAYDLRRRERQSRQTF

SISSMSENGYDPQQNLNDLMLLQLDREANLTSSVTILPLPLQNATVEA

GTRCQVAGWGSQRSGGRLSRFPRFVNVTVTPEDQCRPNNVCTGVLTRR

GGICNGDGGTPLVCEGLAHGVASFSLGPCGRGPDFFTRVALFRDWIDG

VLNNPGPGPA

SH3 domain-binding glutamic acid-rich-like protein

[SEQ ID. NO: 15]

MVIRVYIASSSGSTAIKKKQQDVLGFLEANKIGFEEKDIAANEENRKW

MRENVPENSRPATGYPLPPQIFNESQYRGDYDAFFEARENNAVYAFLG

LTAPPGSKEAEVQAKQQA

-continued

Annexin A5
[SEQ ID. NO: 16]
MAQVLRGTVTDFPGFDERADAETLRKAMKGLGTDEESILTLLTSRSNA
QRQEISAAFKTLFGRDLLDDLKSELTGKFEKLIVALMPSRLYDAYELK
HALKGAGTNEKVLTEIASRTPEELRAIKQVYEEEYGSSLEDDVVGDTS
GYYQRMLVVLLQANRDPDAGIDEAQVEQDAQALFQAGELKWGTDEEKF
ITIFGTRSVSHLRKVFDKYMTISGFQIEETIDRETSGNLEQLLLAVVK
SIRSIPAYLAETLYYAMKGAGTDDHTLIRVMVSRSEIDLFNIRKEFRK
NFATSLYSMIKGDTSGDYKKALLLLCGEDD Interleukin-25
[SEQ ID. NO: 17]
MRERPRLGEDSSLISLFLQVVAFLAMVMGTHTYSHWPSCCPSKGQDTS
EELLRWSTVPVPPLEPARPNRHPESCRASEDGPLNSRAISPWRYELDR
DLNRLPQDLYHARCLCPHCVSLQTGSHMDPRGNSELLYHNQTVFYRRP
CHGEKGTHKGYCLERRLYRVSLACVCVRPRVMG Tubulin folding cofactor B
[SEQ ID. NO: 18]
MEVTGVSAPTVTVFISSSLNTFRSEKRYSRSLTIAEFKCKLELLVGSP
ASCMELELYGVDDKFYSKLDQEDALLGSYPVDDGCRIHVIDHSGARLG
EYEDVSRVEKYTISQEAYDQRQDTVRSFLKRSKLGRYNEEERAQQEAE
AAQRLAEEKAQASSIPVGSRCEVRAAGQSPRRGTVMYVGLTDFKPGYW
IGVRYDEPLGKNDGSVNGKRYFECQAKYGAFVKPAWTVGDFPEEDYGL
DEI Superoxide dismutase [Mn], mitochondrial
[SEQ ID. NO: 19]
MLSRAVCGTSRQLAPALGYLGSRQKHSLPDLPYDYGALEPHINAQIMQ
LHHSKHHAAYVNNLNVTEEKYQEALAKGDVTAQIALQPALKFNGGGHI
NHSIFWTNLSPNGGGEPKGELLEAIKRDFGSFDKFKEKLTAASVGVQG
SGWGWLGFNKERGHLQIAACPNQDPLQGTTGLIPLLGIDVWEHAYYLQ
YKNVRPDYLKAIWNVINWENVTERYMACKK Hemoglobin chain alpha
[SEQ ID. NO: 4]
VLSPADKTNVKAAWGKVGAHAGEYGAEALERMFLSFPTTKTYFPHFDL
SHGSAQVKGHGKKVADALTNAVAHVDDMPNALSALSDLHAHKLRVDPV
NFKLLSHCLLVTLAAHLPAEFTPAVHASLDKFLASVSTVLTSKYR Hemoglobin chain beta
[SEQ ID. NO: 20]
MVHLTPEEKSAVTALWGKVNVDEVGGEALGRLLVVYPWTQRFFESFGDL
STPDAVMGNPKVKAHGKKVLGAFSDGLAHLDNLKGTFATLSELHCDKL
HVDPENFRLLGNVLVCVLAHHFGKEFTPPVQAAYQKWAGVANALAHKY
H Albumin
[SEQ ID. NO: 21]
MKWVTFISLLFLFSSAYSRGVFRRDAHKSEVAHRFKDLGEENFKALVL
IAFAQYLQQCPFEDHVKLVNEVTEFAKTCVADESAENCDKSLHTLFGD
KLCTVATLRETYGEMADCCAKQEPERNECFLQHKDDNPNLPRLVRPEV
DVMCTAFHDNEETFLKKYLYEIARRHPYFYAPELLFFAKRYKAAFTEC
CQAADKAACLLPKLDELRDEGKASSAKQRLKCASLQKFGERAFKAWAV
ARLSQRFPKAEFAEVSKLVTDLTKVHTECCHGDLLECADDRADLAKYI
CENQDSISSKLKECCEKPLLEKSHCIAEVENDEMPADLPSLAADFVES
KDVCKNYAEAKDVFLGMFLYEYARRHPDYSWLLLRLAKTYETTLEKCC
AAADPHECYAKVFDEFKPLVEEPQNLIKQNCELFEQLGEYKFQNALLV
RYTKKVPQVSTPTLVEVSRNLGKVGSKCCKHPEAKRMPCAEDYLSWLN
QLCVLHEKTPVSDRVTKCCTESLVNRRPCFSALEVDETYVPKEFNAET
FTFHADICTLSEKERQIKKQTALVELVKHKPKATKEQLKAVMDDFAAF
VEKCCKADDKETCFAEEGKKLVAASQAALGL Hypothetical Proteins (Putative Proteins with Unknown Function and No Conserved Domains):

XP 001717485 [gi:169170953]
[SEQ ID. NO: 22]
mepqvekchk agneerdqvl adarprrccv veapgpmprg
wilpgarsee rgarlaesrg rgvtprasws rqpaggplss
eghllplvqr dgglaehrg regeegvrag gggtgevrgg
gspgrqpvgr aavtgeagag aagrgaqsvr gpgverrvae
gaqqfgprvg lrqhaerver aqraaegrgg gggggcgaqa
hrrvvgqgqv rwegvgqaar grrmahhcsq grnsqsrhqp
grdrphhhhl eleslrervp ceppppplppl llgvslppfg
lptsasepdp aqrvqstgvy rhrhtnaiev glpgsdkviw
tsdrranwse gcstraaqvg rnftvlygll asappcllhp
ashklpgsaf dlalawgkcl praieafpeq lkhwvlgvsf
espksrtcir plstphsrhc chpqsrqcqn tvgdprqnad
srescsvplv tplgerkwin rnvchseder kpaangsavm
rqmalsfpqp gfilrwlfvq evafpfawts palqslprgs
gtclqkwmaf eveesevaen alkqqsktmf inlawgrrqr
dpevesaekv ggscvtvagt vehfllqtgg ncgfwnsdfe
ecpllstlle wrasplpwgt istlfhpctw vgrmrplspr
avsdarepge vgirgarheg rvahregpqg aatwrdcaip
aqkpggesvr vsfrgcclep legpfpswel vgrlvlsprp
lsapsaprrl gdkaqlpncc lgapptadrq rrksrrvpas
llaripricp eqrpqspipr gqpvppgpmr plseldpkrd
g LOC286076 [gi:119602615]
[SEQ ID. NO: 23]
rscaglnvns rdvgdalprq mmvscpsglp cswwphhpgl
thwmvgpqsr yppgcrlstl lsrapglrve qgvpplalpq
ggarpcsaav rllllavfps ntqaslpasw vaeegqvhrk
glgrewwghl pglcvsaqht cvqckvhqd MSTP132 [gi:33338088]
[SEQ ID. NO: 24]
mkflflfflr qslalsprle csgavlahck lclpglrhcp
apatreaear ewletrsrrl q

TABLE 2 list of 42 identified proteins with differential expression in lymph node positive vs lymph node negative breast cancers with their mass and abundance.

| | M/Z | p | Mean Node Neg | SD Node Neg | Mean Node Pos | SD Node Pos |
|---|---|---|---|---|---|---|
| | | | Cation exchange array (CM10) at pH 4 | | | |
| (1−) | 1375.29 | 0.0274231560 | 1.6870778082 | 1.2081885850 | 0.5747679441 | 0.4389184727 |
| (2+) | 3354.63 | 0.0274231560 | 2.2347285918 | 1.6887134531 | 6.9437801790 | 4.4907141129 |
| (3+) | 3417.37 | 0.0208625840 | 0.9663390866 | 1.6011746950 | 3.3320495713 | 1.7872618804 |
| (4−) | 11506.39 | 0.0023220952 | 8.8690793963 | 4.8298523932 | 2.1522273533 | 2.3582952114 |
| (5−) | 13929.03 | 0.0117186872 | 10.5366148929 | 2.3993891730 | 6.2380287997 | 4.1792723906 |
| (6−) | 14132.43 | 0.0356919017 | 9.1879893115 | 3.6571443298 | 5.3188255848 | 2.8375150991 |
| | | | Anion exchange array (Q10) at pH 9 | | | |
| (7−) | 2022.23 | 0.0086515430 | 17.4659791576 | 5.8218885339 | 9.2959804930 | 3.5399548605 |
| (8−) | 2276.73 | 0.0117186872 | 14.3831923660 | 3.1072477675 | 9.6161770954 | 3.5788505139 |
| (9+) | 2290.00 | 0.0032758984 | 2.2166854670 | 3.6424423991 | 10.7050979707 | 5.2028762498 |
| (10+) | 2306.00 | 0.0459993685 | 11.1330189198 | 9.9884291821 | 20.0282462422 | 8.3634075261 |
| (11+) | 2452.63 | 0.0045744406 | 1.4383931734 | 2.3578200516 | 7.9656949689 | 3.5970398215 |
| (12+) | 2477.81 | 0.0356919017 | 14.1500466740 | 17.6713561306 | 36.8321826002 | 7.5966537307 |
| (13+) | 2662.54 | 0.0356919017 | 2.8656087379 | 4.5177850422 | 7.5039178253 | 3.3615362423 |
| (14+) | 4962.61 | 0.0459993685 | 4.8498450505 | 4.1563158900 | 9.0363313941 | 3.3040218277 |
| (15+) | 7567.26 | 0.0063229490 | 6.5571119856 | 5.3679943679 | 16.8135687049 | 4.5206197829 |
| (16−) | 10280.33 | 0.0274231560 | 11.1977858348 | 2.2602955769 | 8.5119496408 | 1.9923464213 |
| (17−) | 10392.05 | 0.0157143515 | 9.5816337993 | 4.3998366831 | 4.5719291359 | 1.2908014463 |
| (18+) | 11062.03 | 0.0208625840 | 4.7681903768 | 3.2600949614 | 8.7840518433 | 2.3786735179 |
| (19−) | 11298.92 | 0.0007775308 | 11.8128854619 | 3.0102875317 | 3.8806684148 | 2.5876764310 |
| (20−) | 11477.52 | 0.0023220952 | 11.8898141013 | 4.3697538534 | 4.8647728730 | 2.5127084368 |
| (21−) | 12632.05 | 0.0157143515 | 6.9212582463 | 1.9425018406 | 12.2737141087 | 5.7795017397 |
| (22+) | 12787.06 | 0.0032758984 | 3.6624423020 | 1.3195209478 | 6.5246207838 | 1.8522777909 |
| (23−) | 14144.07 | 0.0208625840 | 4.2270909245 | 1.5507169974 | 2.8691794061 | 0.9884474696 |
| (24−) | 14603.70 | 0.0063229490 | 7.3546682643 | 2.4592351470 | 4.6153323662 | 0.5503777087 |
| (25−) | 14754.71 | 0.0063229490 | 5.5556544556 | 2.0759324297 | 3.2513011167 | 0.8662145658 |
| (26−) | 14956.22 | 0.0459993685 | 8.8314709597 | 6.9171022855 | 1.7485547241 | 1.4265824092 |
| (27−) | 15094.45 | 0.0274231560 | 7.4459107443 | 5.1010413462 | 2.1747819723 | 1.0934166759 |
| (28+) | 15110.53 | 0.0007775308 | 14.1776414059 | 9.6032549550 | 34.7866778849 | 5.0110162014 |
| (29−) | 15249.32 | 0.0016291868 | 12.4649281795 | 5.2096509604 | 31.0375434707 | 8.7260256885 |
| (30+) | 15305.01 | 0.0157143515 | 6.1528096689 | 3.3161518043 | 10.7849203112 | 2.2495106869 |
| (31−) | 16888.72 | 0.0086515430 | 8.8036737906 | 2.2257267091 | 5.9527904853 | 1.0006268348 |
| (32−) | 17871.94 | 0.0086515430 | 2.5037287174 | 0.6786425078 | 1.4153589592 | 0.5810624669 |
| (33−) | 18003.62 | 0.0045744406 | 4.5593958506 | 1.1515963754 | 2.6796990848 | 1.1338140961 |
| (34−) | 33356.20 | 0.0459993685 | 2.9463086499 | 0.8967372530 | 2.1736540870 | 0.4838099592 |
| (35−) | 41665.94 | 0.0208625840 | 1.4622985955 | 0.4003093585 | 0.9312387135 | 0.2875171683 |
| | | | Copper loaded Immobilized Metal Affinity array (IMAC-Cu) at 0.1 M Sodium Phosphate/ 0.5 M Sodium Chloride, pH 7 | | | |
| (36+) | 2594.39 | 0.0032758984 | 1.6217419082 | 1.3245833913 | 3.4197868940 | 0.4991381175 |
| (37+) | 3931.77 | 0.0032758984 | 1.0621999969 | 0.7602188469 | 2.6565595811 | 1.3290851933 |
| (38+) | 4115.14 | 0.0032758984 | 1.1469489288 | 0.5049786548 | 4.6782890879 | 4.6910319099 |
| (39+) | 5186.79 | 0.0157143515 | 2.2625664937 | 1.7964215156 | 4.9045423262 | 1.0741129522 |
| (40+) | 9846.03 | 0.0086515430 | 3.1861852181 | 1.8416940282 | 7.6295131435 | 3.2963117374 |
| (41−) | 11304.9 | 0.0157143515 | 5.8771415649 | 3.8176199984 | 2.3282098421 | 1.8146208213 |
| (42−) | 11460.7 | 0.0117186872 | 17.5715851738 | 7.0610563265 | 7.1779059675 | 5.6281725626 |

The "+" and "−" codes refers to an increase or decrease of the abundance of the protein compared to lymph node negative samples.

The invention claimed is:

1. An in vitro method for the prediction, prognosis or diagnosis of metastasis in a patient comprising measuring the level of the proteins Hemoglobin Chain alpha, Eosinophil peroxidase, Histone H4 and 60S ribosomal protein L32 in a biological sample of said patient, wherein said level of proteins is measured by a method selected from a chromatographic method, an electrophoretic method or an immunological assay.

2. The method according to claim 1, comprising the steps of:
   (i) extracting said proteins from a biological sample isolated from said patient; and
   (ii) determining the relative abundance of said proteins in said extract by comparing said abundance to the abundance of said proteins in a reference sample or a reference expression profile; wherein said relative abundance of said proteins is indicative of metastasis.

3. The method according to claim 2 wherein in step (ii) said reference sample or reference expression profile is of a patient not having metastasis; and wherein the increase of said relative abundance compared to said reference sample or reference expression profile is indicative of metastasis.

4. The method of claim 3, wherein said increase indicative of metastasis is at least a two-fold increase.

5. The method of claim 1, wherein the patient is a breast cancer patient.

6. The method of claim 1, wherein the metastasis is lymph node metastasis.

7. The method according to claim 1, wherein said level of proteins is measured using antibodies specific for said proteins.

8. The method of claim 1, wherein said biological sample is a breast tumour sample.

9. The method according to claim 1, further comprising measuring the levels of proteins SEQ ID NO:22, SEQ ID NO:23, SEQ ID NO:24, Hemopexin, Protein DJ-1, Transgelin, Apolipoprotein. A-I, Cellular retinoic acid-binding protein 1, mitochondrial 60 kDa heat shock protein, Heat shock 70 kDa protein, mitochondrial Stress-70 protein, Azurocidin, SH3 domain-binding glutamic acid-rich-like protein, Annexin A5, Interleukin-25, Tubulin folding cofactor B, mitochondrial Superoxide dismutase [Mn], Hemoglobin chain beta and Albumin.

10. The method of claim 9, further comprising measuring the level of SEQ ID NO:1 in a biological sample of said patient.

11. The method of claim 9, further comprising measuring the level of Vascular Endothelial Growth Factor A isoform 111.

12. The method of claim 9, further comprising measuring the level of one or more proteins selected from the group consisting of SEQ ID NO:1, SEQ ID. NO:2, SEQ ID. NO:3, SEQ ID. NO:4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO:14, SEQ ID NO: 15 SEQ ID NO: 16, SEQ ID NO: 17, SEQ ID NO: 18, SEQ ID NO: 19, SEQ ID NO:20 and SEQ ID NO:21.

13. The method according to claim 9, further comprising determining the expression of an oncogene in a biological sample isolated from said patient.

14. The method of claim 1, wherein said method of measuring the level of said proteins is selected from the group consisting of (HP)LC, FPLC, TLC, 1D or 2D protein electrophoresis, enzyme-linked immunosorbent assays (ELISA), immunoblotting, immunospotting, radioimmunoassays, fluid or gel precipitation reactions, immunodiffusion (single or double), agglutination assays, immunoelectrophoresis, time-resolved immunofluorometric assay (TRIFMA), Western blots, liposome immunoassays, complement-fixation assays, immunoradiometric assays, fluorescent immunoassays, protein A immunoassays and immunoPCR.

15. The method of claim 14, wherein said method of measuring the proteins comprises performing protein chip retention chromatography coupled to mass spectrometry.

16. An in vitro method for the prediction, prognosis or diagnosis of metastasis in a patient comprising measuring the level of expression of proteins at the RNA level in a biological sample of said patient, wherein said proteins are Hemoglobin Chain alpha, Eosinophil peroxidase, Histone H4, and 60S ribosomal protein L32, and wherein said level of said proteins is measured by a method selected from Northern blot analysis, real-time PCR or kinetic RT-PCR.

* * * * *

SEQUENCE LISTING

<160> NUMBER OF SEQ ID NOS: 24

<210> SEQ ID NO 1
<211> LENGTH: 20
<212> TYPE: PRT
<213> ORGANISM: Homo sapiens

<400> SEQUENCE: 1

Glu Glu Thr Arg Gly Val Leu Lys Val Phe Leu Glu Asn Val Ile Arg
1               5                   10                  15

Asp Ala Val Thr
            20

-continued

```
<210> SEQ ID NO 2
<211> LENGTH: 21
<212> TYPE: PRT
<213> ORGANISM: Homo sapiens

<400> SEQUENCE: 2

Asn Ile Gly Tyr Gly Ser Asn Lys Lys Thr Lys His Met Leu Pro Ser
1               5                   10                  15

Gly Phe Arg Lys Phe
            20

<210> SEQ ID NO 3
<211> LENGTH: 21
<212> TYPE: PRT
<213> ORGANISM: Homo sapiens

<400> SEQUENCE: 3

Trp Leu Pro Ala Glu Tyr Glu Asp Gly Leu Ser Leu Pro Phe Gly Trp
1               5                   10                  15

Thr Pro Ser Arg Arg
            20

<210> SEQ ID NO 4
<211> LENGTH: 141
<212> TYPE: PRT
<213> ORGANISM: Homo sapiens

<400> SEQUENCE: 4

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
        50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 5
<211> LENGTH: 111
<212> TYPE: PRT
<213> ORGANISM: Homo sapiens

<400> SEQUENCE: 5

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
```

-continued

```
            50                  55                  60
Gly Leu Glu Cys Val Pro Thr Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Cys Asp Lys Pro Arg Arg
                100                 105                 110

<210> SEQ ID NO 6
<211> LENGTH: 462
<212> TYPE: PRT
<213> ORGANISM: Homo sapiens

<400> SEQUENCE: 6

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
                20                  25                  30

Gly Asn Val Ala Glu Gly Glu Thr Lys Pro Asp Pro Asp Val Thr Glu
                35                  40                  45

Arg Cys Ser Asp Gly Trp Ser Phe Asp Ala Thr Thr Leu Asp Asp Asn
                50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
                100                 105                 110

Gly Asp Lys Val Trp Val Tyr Pro Pro Glu Lys Lys Glu Lys Gly Tyr
                115                 120                 125

Pro Lys Leu Leu Gln Asp Glu Phe Pro Gly Ile Pro Ser Pro Leu Asp
                130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
                180                 185                 190

Arg Trp Leu Gly Arg Tyr Tyr Cys Phe Gln Gly Asn Gln Phe Leu Arg
                195                 200                 205

Phe Asp Pro Val Arg Gly Glu Val Pro Pro Arg Tyr Pro Arg Asp Val
                210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255

Cys Ser Pro His Leu Val Leu Ser Ala Leu Thr Ser Asp Asn His Gly
                260                 265                 270

Ala Thr Tyr Ala Phe Ser Gly Thr His Tyr Trp Arg Leu Asp Thr Ser
                275                 280                 285

Arg Asp Gly Trp His Ser Trp Pro Ile Ala His Gln Trp Pro Gln Gly
                290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
```

-continued

```
                    325                 330                 335
Leu Val Ser Gly Tyr Pro Lys Arg Leu Glu Lys Glu Val Gly Thr Pro
                340                 345                 350

His Gly Ile Ile Leu Asp Ser Val Asp Ala Ala Phe Ile Cys Pro Gly
            355                 360                 365

Ser Ser Arg Leu His Ile Met Ala Gly Arg Arg Leu Trp Trp Leu Asp
        370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
                405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
        435                 440                 445

Pro Gln Pro Gln Asn Val Thr Ser Leu Leu Gly Cys Thr His
    450                 455                 460

<210> SEQ ID NO 7
<211> LENGTH: 189
<212> TYPE: PRT
<213> ORGANISM: Homo sapiens

<400> SEQUENCE: 7

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185

<210> SEQ ID NO 8
<211> LENGTH: 201
<212> TYPE: PRT
<213> ORGANISM: Homo sapiens

<400> SEQUENCE: 8

Met Ala Asn Lys Gly Pro Ser Tyr Gly Met Ser Arg Glu Val Gln Ser
1               5                   10                  15
```

```
Lys Ile Glu Lys Lys Tyr Asp Glu Glu Leu Glu Glu Arg Leu Val Glu
             20                  25                  30

Trp Ile Ile Val Gln Cys Gly Pro Asp Val Gly Arg Pro Asp Arg Gly
         35                  40                  45

Arg Leu Gly Phe Gln Val Trp Leu Lys Asn Gly Val Ile Leu Ser Lys
     50                  55                  60

Leu Val Asn Ser Leu Tyr Pro Asp Gly Ser Lys Pro Val Lys Val Pro
65                  70                  75                  80

Glu Asn Pro Pro Ser Met Val Phe Lys Gln Met Glu Gln Val Ala Gln
                 85                  90                  95

Phe Leu Lys Ala Ala Glu Asp Tyr Gly Val Ile Lys Thr Asp Met Phe
            100                 105                 110

Gln Thr Val Asp Leu Phe Glu Gly Lys Asp Met Ala Ala Val Gln Arg
        115                 120                 125

Thr Leu Met Ala Leu Gly Ser Leu Ala Val Thr Lys Asn Asp Gly His
130                 135                 140

Tyr Arg Gly Asp Pro Asn Trp Phe Met Lys Lys Ala Gln Glu His Lys
145                 150                 155                 160

Arg Glu Phe Thr Glu Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
        195                 200

<210> SEQ ID NO 9
<211> LENGTH: 267
<212> TYPE: PRT
<213> ORGANISM: Homo sapiens

<400> SEQUENCE: 9

Met Lys Ala Ala Val Leu Thr Leu Ala Val Leu Phe Leu Thr Gly Ser
1               5                  10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190
```

```
Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 10
<211> LENGTH: 137
<212> TYPE: PRT
<213> ORGANISM: Homo sapiens

<400> SEQUENCE: 10

Met Pro Asn Phe Ala Gly Thr Trp Lys Met Arg Ser Ser Glu Asn Phe
1               5                   10                  15

Asp Glu Leu Leu Lys Ala Leu Gly Val Asn Ala Met Leu Arg Lys Val
            20                  25                  30

Ala Val Ala Ala Ser Lys Pro His Val Glu Ile Arg Gln Asp Gly
        35                  40                  45

Asp Gln Phe Tyr Ile Lys Thr Ser Thr Thr Val Arg Thr Thr Glu Ile
    50                  55                  60

Asn Phe Lys Val Gly Glu Gly Phe Glu Glu Thr Val Asp Gly Arg
65                  70                  75                  80

Lys Cys Arg Ser Leu Ala Thr Trp Glu Asn Glu Asn Lys Ile His Cys
                85                  90                  95

Thr Gln Thr Leu Leu Glu Gly Asp Gly Pro Lys Thr Tyr Trp Thr Arg
            100                 105                 110

Glu Leu Ala Asn Asp Glu Leu Ile Leu Thr Phe Gly Ala Asp Asp Val
        115                 120                 125

Val Cys Thr Arg Ile Tyr Val Arg Glu
    130                 135

<210> SEQ ID NO 11
<211> LENGTH: 573
<212> TYPE: PRT
<213> ORGANISM: Homo sapiens

<400> SEQUENCE: 11

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110
```

```
Thr Thr Thr Ala Thr Val Leu Ala Arg Ser Ile Ala Lys Glu Gly Phe
        115                 120                 125
Glu Lys Ile Ser Lys Gly Ala Asn Pro Val Glu Ile Arg Arg Gly Val
130                 135                 140
Met Leu Ala Val Asp Ala Val Ile Ala Glu Leu Lys Lys Gln Ser Lys
145                 150                 155                 160
Pro Val Thr Thr Pro Glu Glu Ile Ala Gln Val Ala Thr Ile Ser Ala
                165                 170                 175
Asn Gly Asp Lys Glu Ile Gly Asn Ile Ile Ser Asp Ala Met Lys Lys
                180                 185                 190
Val Gly Arg Lys Gly Val Ile Thr Val Lys Asp Gly Lys Thr Leu Asn
                195                 200                 205
Asp Glu Leu Glu Ile Ile Glu Gly Met Lys Phe Asp Arg Gly Tyr Ile
210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Ile Gln Ser
                245                 250                 255
Ile Val Pro Ala Leu Glu Ile Ala Asn Ala His Arg Lys Pro Leu Val
                260                 265                 270
Ile Ile Ala Glu Asp Val Asp Gly Glu Ala Leu Ser Thr Leu Val Leu
                275                 280                 285
Asn Arg Leu Lys Val Gly Leu Gln Val Val Ala Val Lys Ala Pro Gly
                290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Thr Leu Asn Leu Glu Asp
                325                 330                 335
Val Gln Pro His Asp Leu Gly Lys Val Gly Glu Val Ile Val Thr Lys
                340                 345                 350
Asp Asp Ala Met Leu Leu Lys Gly Lys Gly Asp Lys Ala Gln Ile Glu
                355                 360                 365
Lys Arg Ile Gln Glu Ile Ile Glu Gln Leu Asp Val Thr Thr Ser Glu
370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
                420                 425                 430
Glu Glu Gly Ile Val Leu Gly Gly Gly Cys Ala Leu Leu Arg Cys Ile
                435                 440                 445
Pro Ala Leu Asp Ser Leu Thr Pro Ala Asn Glu Asp Gln Lys Ile Gly
                450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
                500                 505                 510
Met Val Glu Lys Gly Ile Ile Asp Pro Thr Lys Val Val Arg Thr Ala
                515                 520                 525
Leu Leu Asp Ala Ala Gly Val Ala Ser Leu Leu Thr Thr Ala Glu Val
530                 535                 540
```

-continued

```
Val Val Thr Glu Ile Pro Lys Glu Lys Asp Pro Gly Met Gly Ala
545                 550                 555                 560

Met Gly Gly Met Gly Gly Gly Met Gly Gly Gly Met Phe
                565                 570

<210> SEQ ID NO 12
<211> LENGTH: 641
<212> TYPE: PRT
<213> ORGANISM: Homo sapiens

<400> SEQUENCE: 12

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
            195                 200                 205

Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
                340                 345                 350
```

-continued

```
Phe Phe Asn Gly Arg Asp Leu Asn Lys Ser Ile Asn Pro Asp Glu Ala
            355                 360                 365
Val Ala Tyr Gly Ala Ala Val Gln Ala Ile Leu Met Gly Asp Lys
    370                 375                 380
Ser Glu Asn Val Gln Asp Leu Leu Leu Asp Val Ala Pro Leu Ser
385                 390                 395                 400
Leu Gly Leu Glu Thr Ala Gly Gly Val Met Thr Ala Leu Ile Lys Arg
                405                 410                 415
Asn Ser Thr Ile Pro Thr Lys Gln Thr Gln Ile Phe Thr Thr Tyr Ser
                420                 425                 430
Asp Asn Gln Pro Gly Val Leu Ile Gln Val Tyr Glu Gly Glu Arg Ala
            435                 440                 445
Met Thr Lys Asp Asn Asn Leu Leu Gly Arg Phe Glu Leu Ser Gly Ile
    450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Thr Ala Thr Asp Lys Ser Thr Gly
                485                 490                 495
Lys Ala Asn Lys Ile Thr Ile Thr Asn Asp Lys Gly Arg Leu Ser Lys
                500                 505                 510
Glu Glu Ile Glu Arg Met Val Gln Glu Ala Lys Tyr Lys Ala Glu
            515                 520                 525
Asp Glu Val Gln Arg Glu Arg Val Ser Ala Lys Asn Ala Leu Glu Ser
    530                 535                 540
Tyr Ala Phe Asn Met Lys Ser Ala Val Glu Asp Glu Gly Leu Lys Gly
545                 550                 555                 560
Lys Ile Ser Glu Ala Asp Lys Lys Lys Val Leu Asp Lys Cys Gln Glu
                565                 570                 575
Val Ile Ser Trp Leu Asp Ala Asn Thr Leu Ala Glu Lys Asp Glu Phe
                580                 585                 590
Glu His Lys Arg Lys Glu Leu Glu Gln Val Cys Asn Pro Ile Ile Ser
            595                 600                 605
Gly Leu Tyr Gln Gly Ala Gly Gly Pro Gly Pro Gly Gly Phe Gly Ala
    610                 615                 620
Gln Gly Pro Lys Gly Gly Ser Gly Ser Gly Pro Thr Ile Glu Glu Val
625                 630                 635                 640
Asp
```

<210> SEQ ID NO 13
<211> LENGTH: 679
<212> TYPE: PRT
<213> ORGANISM: Homo sapiens

<400> SEQUENCE: 13

```
Met Ile Ser Ala Ser Arg Ala Ala Ala Arg Leu Val Gly Ala Ala
1               5                   10                  15
Ala Ser Arg Gly Pro Thr Ala Arg His Gln Asp Ser Trp Asn Gly
            20                  25                  30
Leu Ser His Glu Ala Phe Arg Leu Val Ser Arg Arg Asp Tyr Ala Ser
        35                  40                  45
Glu Ala Ile Lys Gly Ala Val Val Gly Ile Asp Leu Gly Thr Thr Asn
    50                  55                  60
Ser Cys Val Ala Val Met Glu Gly Lys Gln Ala Lys Val Leu Glu Asn
65                  70                  75                  80
```

-continued

```
Ala Glu Gly Ala Arg Thr Thr Pro Ser Val Val Ala Phe Thr Ala Asp
                85                  90                  95
Gly Glu Arg Leu Val Gly Met Pro Ala Lys Arg Gln Ala Val Thr Asn
            100                 105                 110
Pro Asn Asn Thr Phe Tyr Ala Thr Lys Arg Leu Ile Gly Arg Arg Tyr
        115                 120                 125
Asp Asp Pro Glu Val Gln Lys Asp Ile Lys Asn Val Pro Phe Lys Ile
    130                 135                 140
Val Arg Ala Ser Asn Gly Asp Ala Trp Val Glu Ala His Gly Lys Leu
145                 150                 155                 160
Tyr Ser Pro Ser Gln Ile Gly Ala Phe Val Leu Met Lys Met Lys Glu
                165                 170                 175
Thr Ala Glu Asn Tyr Leu Gly His Thr Ala Lys Asn Ala Val Ile Thr
            180                 185                 190
Val Pro Ala Tyr Phe Asn Asp Ser Gln Arg Gln Ala Thr Lys Asp Ala
        195                 200                 205
Gly Gln Ile Ser Gly Leu Asn Val Leu Arg Val Ile Asn Glu Pro Thr
    210                 215                 220
Ala Ala Ala Leu Ala Tyr Gly Leu Asp Lys Ser Glu Asp Lys Val Ile
225                 230                 235                 240
Ala Val Tyr Asp Leu Gly Gly Gly Thr Phe Asp Ile Ser Ile Leu Glu
                245                 250                 255
Ile Gln Lys Gly Val Phe Glu Val Lys Ser Thr Asn Gly Asp Thr Phe
            260                 265                 270
Leu Gly Gly Glu Asp Phe Asp Gln Ala Leu Leu Arg His Ile Val Lys
        275                 280                 285
Glu Phe Lys Arg Glu Thr Gly Val Asp Leu Thr Lys Asp Asn Met Ala
    290                 295                 300
Leu Gln Arg Val Arg Glu Ala Ala Glu Lys Ala Lys Cys Glu Leu Ser
305                 310                 315                 320
Ser Ser Val Gln Thr Asp Ile Asn Leu Pro Tyr Leu Thr Met Asp Ser
                325                 330                 335
Ser Gly Pro Lys His Leu Asn Met Lys Leu Thr Arg Ala Gln Phe Glu
            340                 345                 350
Gly Ile Val Thr Asp Leu Ile Arg Arg Thr Ile Ala Pro Cys Gln Lys
        355                 360                 365
Ala Met Gln Asp Ala Glu Val Ser Lys Ser Asp Ile Gly Glu Val Ile
    370                 375                 380
Leu Val Gly Gly Met Thr Arg Met Pro Lys Val Gln Gln Thr Val Gln
385                 390                 395                 400
Asp Leu Phe Gly Arg Ala Pro Ser Lys Ala Val Asn Pro Asp Glu Ala
                405                 410                 415
Val Ala Ile Gly Ala Ala Ile Gln Gly Gly Val Leu Ala Gly Asp Val
            420                 425                 430
Thr Asp Val Leu Leu Leu Asp Val Thr Pro Leu Ser Leu Gly Ile Glu
        435                 440                 445
Thr Leu Gly Gly Val Phe Thr Lys Leu Ile Asn Arg Asn Thr Thr Ile
    450                 455                 460
Pro Thr Lys Lys Ser Gln Val Phe Ser Thr Ala Ala Asp Gly Gln Thr
465                 470                 475                 480
Gln Val Glu Ile Lys Val Cys Gln Gly Glu Arg Glu Met Ala Gly Asp
                485                 490                 495
Asn Lys Leu Leu Gly Gln Phe Thr Leu Ile Gly Ile Pro Pro Ala Pro
            500                 505                 510
```

```
Arg Gly Val Pro Gln Ile Glu Val Thr Phe Asp Ile Asp Ala Asn Gly
            515                 520                 525

Ile Val His Val Ser Ala Lys Asp Lys Gly Thr Gly Arg Glu Gln Gln
            530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
            610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
            675

<210> SEQ ID NO 14
<211> LENGTH: 251
<212> TYPE: PRT
<213> ORGANISM: Homo sapiens

<400> SEQUENCE: 14

Met Thr Arg Leu Thr Val Leu Ala Leu Leu Ala Gly Leu Leu Ala Ser
1               5                   10                  15

Ser Arg Ala Gly Ser Ser Pro Leu Leu Asp Ile Val Gly Gly Arg Lys
                20                  25                  30

Ala Arg Pro Arg Gln Phe Pro Phe Leu Ala Ser Ile Gln Asn Gln Gly
            35                  40                  45

Arg His Phe Cys Gly Gly Ala Leu Ile His Ala Arg Phe Val Met Thr
        50                  55                  60

Ala Ala Ser Cys Phe Gln Ser Gln Asn Pro Gly Val Ser Thr Val Val
65                  70                  75                  80

Leu Gly Ala Tyr Asp Leu Arg Arg Arg Glu Arg Gln Ser Arg Gln Thr
                85                  90                  95

Phe Ser Ile Ser Ser Met Ser Glu Asn Gly Tyr Asp Pro Gln Gln Asn
                100                 105                 110

Leu Asn Asp Leu Met Leu Leu Gln Leu Asp Arg Glu Ala Asn Leu Thr
            115                 120                 125

Ser Ser Val Thr Ile Leu Pro Leu Pro Leu Gln Asn Ala Thr Val Glu
130                 135                 140

Ala Gly Thr Arg Cys Gln Val Ala Gly Trp Gly Ser Gln Arg Ser Gly
145                 150                 155                 160

Gly Arg Leu Ser Arg Phe Pro Arg Phe Val Asn Val Thr Val Thr Pro
                165                 170                 175

Glu Asp Gln Cys Arg Pro Asn Asn Val Cys Thr Gly Val Leu Thr Arg
            180                 185                 190

Arg Gly Gly Ile Cys Asn Gly Asp Gly Gly Thr Pro Leu Val Cys Glu
        195                 200                 205
```

```
Gly Leu Ala His Gly Val Ala Ser Phe Ser Leu Gly Pro Cys Gly Arg
    210                 215                 220

Gly Pro Asp Phe Phe Thr Arg Val Ala Leu Phe Arg Asp Trp Ile Asp
225                 230                 235                 240

Gly Val Leu Asn Asn Pro Gly Pro Gly Pro Ala
                245                 250

<210> SEQ ID NO 15
<211> LENGTH: 114
<212> TYPE: PRT
<213> ORGANISM: Homo sapiens

<400> SEQUENCE: 15

Met Val Ile Arg Val Tyr Ile Ala Ser Ser Gly Ser Thr Ala Ile
1               5                   10                  15

Lys Lys Lys Gln Gln Asp Val Leu Gly Phe Leu Glu Ala Asn Lys Ile
                20                  25                  30

Gly Phe Glu Glu Lys Asp Ile Ala Ala Asn Glu Glu Asn Arg Lys Trp
                35                  40                  45

Met Arg Glu Asn Val Pro Glu Asn Ser Arg Pro Ala Thr Gly Tyr Pro
50                  55                  60

Leu Pro Pro Gln Ile Phe Asn Glu Ser Gln Tyr Arg Gly Asp Tyr Asp
65                  70                  75                  80

Ala Phe Phe Glu Ala Arg Glu Asn Asn Ala Val Tyr Ala Phe Leu Gly
                85                  90                  95

Leu Thr Ala Pro Pro Gly Ser Lys Glu Ala Glu Val Gln Ala Lys Gln
                100                 105                 110

Gln Ala

<210> SEQ ID NO 16
<211> LENGTH: 320
<212> TYPE: PRT
<213> ORGANISM: Homo sapiens

<400> SEQUENCE: 16

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
                35                  40                  45

Gln Arg Gln Glu Ile Ser Ala Ala Phe Lys Thr Leu Phe Gly Arg Asp
50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
                100                 105                 110

Ile Ile Ala Ser Arg Thr Pro Glu Glu Leu Arg Ala Ile Lys Gln Val
                115                 120                 125

Tyr Glu Glu Glu Tyr Gly Ser Ser Leu Glu Asp Asp Val Val Gly Asp
                130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
```

```
                    165                 170                 175
Gln Ala Leu Phe Gln Ala Gly Glu Leu Lys Trp Gly Thr Asp Glu Glu
                180                 185                 190

Lys Phe Ile Thr Ile Phe Gly Thr Arg Ser Val Ser His Leu Arg Lys
            195                 200                 205

Val Phe Asp Lys Tyr Met Thr Ile Ser Gly Phe Gln Ile Glu Glu Thr
        210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Cys Gly Glu Asp Asp
305                 310                 315                 320

<210> SEQ ID NO 17
<211> LENGTH: 177
<212> TYPE: PRT
<213> ORGANISM: Homo sapiens

<400> SEQUENCE: 17

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
                20                  25                  30

Tyr Ser His Trp Pro Ser Cys Cys Pro Ser Lys Gly Gln Asp Thr Ser
            35                  40                  45

Glu Glu Leu Leu Arg Trp Ser Thr Val Pro Val Pro Pro Leu Glu Pro
        50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
        115                 120                 125

Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly

<210> SEQ ID NO 18
<211> LENGTH: 244
<212> TYPE: PRT
<213> ORGANISM: Homo sapiens

<400> SEQUENCE: 18
```

```
Met Glu Val Thr Gly Val Ser Ala Pro Thr Val Thr Val Phe Ile Ser
1               5                   10                  15

Ser Ser Leu Asn Thr Phe Arg Ser Glu Lys Arg Tyr Ser Arg Ser Leu
            20                  25                  30

Thr Ile Ala Glu Phe Lys Cys Lys Leu Glu Leu Leu Val Gly Ser Pro
        35                  40                  45

Ala Ser Cys Met Glu Leu Glu Leu Tyr Gly Val Asp Asp Lys Phe Tyr
    50                  55                  60

Ser Lys Leu Asp Gln Glu Asp Ala Leu Leu Gly Ser Tyr Pro Val Asp
65                  70                  75                  80

Asp Gly Cys Arg Ile His Val Ile Asp His Ser Gly Ala Arg Leu Gly
                85                  90                  95

Glu Tyr Glu Asp Val Ser Arg Val Glu Lys Tyr Thr Ile Ser Gln Glu
            100                 105                 110

Ala Tyr Asp Gln Arg Gln Asp Thr Val Arg Ser Phe Leu Lys Arg Ser
        115                 120                 125

Lys Leu Gly Arg Tyr Asn Glu Glu Arg Ala Gln Gln Glu Ala Glu
130                 135                 140

Ala Ala Gln Arg Leu Ala Glu Glu Lys Ala Gln Ala Ser Ser Ile Pro
145                 150                 155                 160

Val Gly Ser Arg Cys Glu Val Arg Ala Ala Gly Gln Ser Pro Arg Arg
                165                 170                 175

Gly Thr Val Met Tyr Val Gly Leu Thr Asp Phe Lys Pro Gly Tyr Trp
            180                 185                 190

Ile Gly Val Arg Tyr Asp Glu Pro Leu Gly Lys Asn Asp Gly Ser Val
        195                 200                 205

Asn Gly Lys Arg Tyr Phe Glu Cys Gln Ala Lys Tyr Gly Ala Phe Val
    210                 215                 220

Lys Pro Ala Val Val Thr Val Gly Asp Phe Pro Glu Glu Asp Tyr Gly
225                 230                 235                 240

Leu Asp Glu Ile

<210> SEQ ID NO 19
<211> LENGTH: 222
<212> TYPE: PRT
<213> ORGANISM: Homo sapiens

<400> SEQUENCE: 19

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
```

```
            130                 135                 140
Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
                195                 200                 205

Asn Trp Glu Asn Val Thr Glu Arg Tyr Met Ala Cys Lys Lys
            210                 215                 220

<210> SEQ ID NO 20
<211> LENGTH: 147
<212> TYPE: PRT
<213> ORGANISM: Homo sapiens

<400> SEQUENCE: 20

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 21
<211> LENGTH: 609
<212> TYPE: PRT
<213> ORGANISM: Homo sapiens

<400> SEQUENCE: 21

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95
```

```
Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
```

```
                515                 520                 525
Glu Thr Phe Thr Phe His Ala Asp Ile Cys Thr Leu Ser Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605

Leu

<210> SEQ ID NO 22
<211> LENGTH: 801
<212> TYPE: PRT
<213> ORGANISM: Homo sapiens

<400> SEQUENCE: 22

Met Glu Pro Gln Val Glu Lys Cys His Lys Ala Gly Asn Glu Glu Arg
1               5                   10                  15

Asp Gln Val Leu Ala Asp Ala Arg Pro Arg Arg Cys Cys Val Val Glu
                20                  25                  30

Ala Pro Gly Pro Met Pro Arg Gly Trp Ile Leu Pro Gly Ala Arg Ser
            35                  40                  45

Glu Glu Arg Gly Ala Arg Leu Ala Glu Ser Arg Gly Arg Gly Val Thr
    50                  55                  60

Pro Arg Ala Ser Trp Ser Arg Gln Pro Ala Gly Gly Pro Leu Ser Ser
65                  70                  75                  80

Glu Gly His Leu Leu Pro Leu Val Gln Arg Asp Gly Gly Gly Leu Ala
                85                  90                  95

Glu His Arg Gly Arg Glu Gly Glu Glu Gly Val Arg Ala Gly Gly Gly
                100                 105                 110

Gly Thr Gly Glu Val Arg Gly Gly Gly Ser Pro Gly Arg Gln Pro Val
            115                 120                 125

Gly Arg Ala Ala Val Thr Gly Glu Ala Gly Ala Gly Ala Ala Gly Arg
        130                 135                 140

Gly Ala Gln Ser Val Arg Gly Pro Gly Val Glu Arg Arg Val Ala Glu
145                 150                 155                 160

Gly Ala Gln Gln Phe Gly Pro Arg Val Gly Leu Arg Gln His Ala Glu
                165                 170                 175

Arg Val Glu Arg Ala Gln Arg Ala Ala Glu Gly Arg Gly Gly Gly Gly
                180                 185                 190

Gly Gly Gly Cys Gly Ala Gln Ala His Arg Val Val Gly Gln Gly
            195                 200                 205

Gln Val Arg Trp Glu Gly Val Gly Gln Ala Ala Arg Gly Arg Arg Met
        210                 215                 220

Ala His His Cys Ser Gln Gly Arg Asn Ser Gln Ser Arg His Gln Pro
225                 230                 235                 240

Gly Arg Asp Arg Pro His His His Leu Glu Leu Glu Ser Leu Arg
                245                 250                 255

Glu Arg Val Pro Cys Glu Pro Pro Pro Leu Pro Pro Leu Leu Leu
            260                 265                 270

Gly Val Ser Leu Pro Pro Phe Gly Leu Pro Thr Ser Ala Ser Glu Pro
        275                 280                 285
```

```
Asp Pro Ala Gln Arg Val Gln Ser Thr Gly Val Tyr Arg His Arg His
    290                 295                 300

Thr Asn Ala Ile Glu Val Gly Leu Pro Gly Ser Asp Lys Val Ile Trp
305                 310                 315                 320

Thr Ser Asp Arg Arg Ala Asn Trp Ser Glu Gly Cys Ser Thr Arg Ala
                325                 330                 335

Ala Gln Val Gly Arg Asn Phe Thr Val Leu Tyr Gly Leu Leu Ala Ser
            340                 345                 350

Ala Pro Pro Cys Leu Leu His Pro Ala Ser His Lys Leu Pro Gly Ser
        355                 360                 365

Ala Phe Asp Leu Ala Leu Ala Trp Gly Lys Cys Leu Pro Arg Ala Ile
    370                 375                 380

Glu Ala Phe Pro Glu Gln Leu Lys His Trp Val Leu Gly Val Ser Phe
385                 390                 395                 400

Glu Ser Pro Lys Ser Arg Thr Cys Ile Arg Pro Leu Ser Thr Pro His
                405                 410                 415

Ser Arg His Cys Cys His Pro Gln Ser Arg Gln Cys Gln Asn Thr Val
            420                 425                 430

Gly Asp Pro Arg Gln Asn Ala Asp Ser Arg Glu Ser Cys Ser Val Pro
        435                 440                 445

Leu Val Thr Pro Leu Gly Glu Arg Lys Trp Ile Asn Arg Asn Val Cys
    450                 455                 460

His Ser Glu Asp Glu Arg Lys Pro Ala Ala Asn Gly Ser Ala Val Met
465                 470                 475                 480

Arg Gln Met Ala Leu Ser Phe Pro Gln Pro Gly Phe Ile Leu Arg Trp
                485                 490                 495

Leu Phe Val Gln Glu Val Ala Phe Pro Phe Ala Trp Thr Ser Pro Ala
            500                 505                 510

Leu Gln Ser Leu Pro Arg Gly Ser Gly Thr Cys Leu Gln Lys Trp Met
        515                 520                 525

Ala Phe Glu Val Glu Glu Ser Glu Val Ala Glu Asn Ala Leu Lys Gln
    530                 535                 540

Gln Ser Lys Thr Met Phe Ile Asn Leu Ala Trp Gly Arg Arg Gln Arg
545                 550                 555                 560

Asp Pro Glu Val Glu Ser Ala Glu Lys Val Gly Gly Ser Cys Val Thr
                565                 570                 575

Val Ala Gly Thr Val Glu His Phe Leu Leu Gln Thr Gly Gly Asn Cys
            580                 585                 590

Gly Phe Trp Asn Ser Asp Phe Glu Glu Cys Pro Leu Leu Ser Thr Leu
        595                 600                 605

Leu Glu Trp Arg Ala Ser Pro Leu Pro Trp Gly Thr Ile Ser Thr Leu
    610                 615                 620

Phe His Pro Cys Thr Trp Val Gly Arg Met Arg Pro Leu Ser Pro Arg
625                 630                 635                 640

Ala Val Ser Asp Ala Arg Glu Pro Gly Glu Val Gly Ile Arg Gly Ala
                645                 650                 655

Arg His Glu Gly Arg Val Ala His Arg Glu Gly Pro Gln Gly Ala Ala
            660                 665                 670

Thr Trp Arg Asp Cys Ala Ile Pro Ala Gln Lys Pro Gly Gly Glu Ser
        675                 680                 685

Val Arg Val Ser Phe Arg Gly Cys Cys Leu Glu Pro Leu Glu Gly Pro
    690                 695                 700

Phe Pro Ser Trp Glu Leu Val Gly Arg Leu Val Leu Ser Pro Arg Pro
```

```
                                                705                 710                 715                 720
Leu Ser Ala Pro Ser Ala Pro Arg Arg Leu Gly Asp Lys Ala Gln Leu
                    725                 730                 735

Pro Asn Cys Cys Leu Gly Ala Pro Pro Thr Ala Asp Arg Gln Arg Arg
            740                 745                 750

Lys Ser Arg Arg Val Pro Ala Ser Leu Leu Ala Arg Ile Pro Arg Leu
                755                 760                 765

Cys Pro Glu Gln Arg Pro Gln Ser Pro Ile Pro Arg Gly Gln Pro Val
            770                 775                 780

Pro Pro Gly Pro Met Arg Pro Leu Ser Glu Leu Asp Pro Lys Arg Asp
785                 790                 795                 800

Gly

<210> SEQ ID NO 23
<211> LENGTH: 149
<212> TYPE: PRT
<213> ORGANISM: Homo sapiens

<400> SEQUENCE: 23

Arg Ser Cys Ala Gly Leu Asn Val Asn Ser Arg Asp Val Gly Asp Ala
1               5                   10                  15

Leu Pro Arg Gln Met Met Val Ser Cys Pro Ser Gly Leu Pro Cys Ser
            20                  25                  30

Trp Trp Pro His His Pro Gly Leu Thr His Trp Met Val Gly Pro Gln
        35                  40                  45

Ser Arg Tyr Pro Pro Gly Cys Arg Leu Ser Thr Leu Leu Ser Arg Ala
    50                  55                  60

Pro Gly Leu Arg Val Glu Gln Gly Val Pro Leu Ala Leu Pro Gln
65                  70                  75                  80

Gly Gly Ala Arg Pro Cys Ser Ala Ala Val Arg Leu Leu Leu Ala
                85                  90                  95

Val Phe Pro Ser Asn Thr Gln Ala Ser Leu Pro Ala Ser Trp Val Ala
            100                 105                 110

Glu Glu Gly Gln Val His Arg Lys Gly Leu Gly Arg Glu Trp Trp Gly
        115                 120                 125

His Leu Pro Gly Leu Cys Val Ser Ala Gln His Thr Cys Val Gln Cys
    130                 135                 140

Lys Val His Gln Asp
145

<210> SEQ ID NO 24
<211> LENGTH: 61
<212> TYPE: PRT
<213> ORGANISM: Homo sapiens

<400> SEQUENCE: 24

Met Lys Phe Leu Phe Leu Phe Leu Arg Gln Ser Leu Ala Leu Ser
1               5                   10                  15

Pro Arg Leu Glu Cys Ser Gly Ala Val Leu Ala His Cys Lys Leu Cys
            20                  25                  30

Leu Pro Gly Leu Arg His Cys Pro Ala Pro Ala Thr Arg Glu Ala Glu
        35                  40                  45

Ala Arg Glu Trp Leu Glu Thr Arg Ser Arg Arg Leu Gln
    50                  55                  60
```